United States Patent [19]
Della Valle et al.

[11] Patent Number: 5,676,964
[45] Date of Patent: Oct. 14, 1997

[54] CROSSLINKED CARBOXY POLYSACCHARIDES

[75] Inventors: Francesco Della Valle, Padua; Aurelio Romeo, Rome, both of Italy

[73] Assignee: Fidia, S.p.A., Abano Terme, Italy

[21] Appl. No.: 465,055

[22] Filed: Jun. 5, 1995

Related U.S. Application Data

[63] Continuation of Ser. No. 70,505, Jun. 1, 1993, which is a continuation of Ser. No. 350,919, May 12, 1989, abandoned.

[30] Foreign Application Priority Data

May 13, 1988 [IT] Italy ...................... 47964/88

[51] Int. Cl.$^6$ .............. A61F 2/00; A61K 31/70; C07H 5/04
[52] U.S. Cl. .......... 424/423; 424/401; 424/408; 424/422; 514/54; 514/178; 514/181; 514/453; 536/53; 536/55; 536/55.1; 536/115; 536/119
[58] Field of Search ............. 514/54, 171, 178, 514/181, 453, 463; 424/401, 408, 422, 443, 423, 463, 483, 584; 536/53, 55, 55.1, 115, 119

[56] References Cited

U.S. PATENT DOCUMENTS

| | | | |
|---|---|---|---|
| 2,481,804 | 9/1949 | Whittingham | 514/54 |
| 3,792,164 | 2/1974 | Bechtold | 514/54 |
| 4,141,973 | 2/1979 | Balazs | 514/54 |
| 4,521,594 | 6/1985 | Kanematu | 536/98 |
| 4,582,865 | 4/1986 | Balazs et al. | 514/29 |
| 4,605,691 | 8/1986 | Balazs et al. | 524/27 |
| 4,636,524 | 1/1987 | Balazs et al. | 514/781 |
| 4,713,448 | 12/1987 | Balazs et al. | 536/55.1 |
| 4,716,154 | 12/1987 | Malson et al. | 514/54 |
| 4,736,024 | 4/1988 | Della Valle et al. | 536/55.3 |
| 4,772,419 | 9/1988 | Malson et al. | 252/315.1 |
| 4,801,619 | 1/1989 | Lindblad | 514/42 |
| 4,822,598 | 4/1989 | Lang et al. | 424/47 |
| 4,851,521 | 7/1989 | Della Valle et al. | 424/423 |
| 4,937,270 | 6/1990 | Hamilton et al. | 514/777 |
| 4,957,744 | 9/1990 | della Valle et al. | 424/401 |
| 4,963,666 | 10/1990 | Mälson | 536/55.1 |
| 5,017,229 | 5/1991 | Burns et al. | 106/162.2 |

FOREIGN PATENT DOCUMENTS

| | | |
|---|---|---|
| 61-00017 | 1/1986 | Japan. |
| 1042864 | 9/1966 | United Kingdom. |
| 1086323 | 10/1967 | United Kingdom. |
| 8600079 | 1/1986 | WIPO. |
| 8707898 | 12/1987 | WIPO. |

OTHER PUBLICATIONS

Darke et al., J. Mol. Biol., pp. 477–486 (1975).
Morris et al., J. Mol. Biol., 138, pp. 383–400 (1980).
Park et al., Biopolymers, 17, pp. 1323–1333 (1978).
Atkins et al., Int. J. Biol. Macromol., 2, 318–319 (1980).
Sheehan et al., Int. J. Biol. Macromol., 5, 215–221 (1983).
Turner et al., Archives of Biochemistry and Biophysics, 265, pp. 484–495 (1988).
Heatley et al., Biochem. J., 254, pp. 489–493 (1988).
Scott, Ciba Foundation Symposium 143, The Biology of Hyaluronan, ed. John Wiley & Sons (1989).
Kvam et al., Carbohydrate Research, 230, pp. 1–13 (1992).
Bodanszky, Int. J. Peptide Protein Res., 25, 449–474 (1985).
Gross et al., The Peptides, vol. 1, Chapter 2, 66–104 (1979).
Keller, Biochim. Biophys. Acta 148:757–766 (1967).
Balazs et al., Chemical Abstract 103:200894b (1985).
Balazs et al., Chemical Abstracts 104:95518c (1986).
Peyman et al., International Ophthalmology 10:133–141 (1987).
Jeanloz et al., Studies on Hyaluronic Acid and Related Substances, 495–511 (1949).
Pigman et al., Biochem. Biophys. Acta, vol. 53, 254–262 (1961).
Pigman et al., Archives of Biochemistry & Biophysics, vol. 89, 184–193 (1960).
Bothner et al., Int. J. Biol. Nacromol., vol. 10, 287–291 (1988).
Wedlock et al., Int. J. Biol. Macromol., vol. 5, 186–188 (1983).
Atkins et al., Biochemical Journal, 22, p. 1255 (1972).

*Primary Examiner*—Elli Peselev
*Attorney, Agent, or Firm*—Birch, Stewart, Kolasch & Birch, LLP

[57] ABSTRACT

Inter and/or intramolecular cross-linked esters of acid polysaccharides are disclosed in which a part or all of the carboxy groups are esterified with hydroxyl groups of the same molecule and/or of different molecules of the acid polysaccharide. These inner cross-linked esters of polysaccharide acids are useful in the field of biodegradable plastic materials, to manufacture sanitary and surgical articles, in the cosmetic and pharmaceutical fields, in the food industry and in many other industrial fields.

65 Claims, No Drawings

CROSSLINKED CARBOXY POLYSACCHARIDES

This application is a continuation of application Ser. No. 08/070,505, filed on Jun. 1, 1993, which is a continuation of application Ser. No. 07/350,919 filed May 12, 1989, now abandoned, the entire contents of which are hereby incorporated by reference.

SUMMARY

The present invention concerns inter and/or intramolecular esters of acid polysaccharides containing carboxy functions, in which a part or all of such functions are esterified with hydroxyl groups of the same molecule and/or of different molecules of the acid polysaccharide, thus forming lactone or intermolecular ester bonds. These "inner" esters of polysaccharide acids, in which there is no intervention by OH groups of other alcohols, can also be defined as "auto-crosslinked polysaccharides", since the formation of a mono- or polymolecular cross-link is the consequence of the abovementioned internal esterification. Hereafter, the new compounds of the present invention will be referred to by this definition. The adjective "cross-linked" refers to the crosswise connections between the carboxyls and hydroxyls of the polysaccharide molecules.

The new inner esters can be total or partial, depending on whether all or only part of the carboxy functions are esterified in the above manner. In the partial inner esters, further carboxy functions can be either totally or partially esterified with monovalent or polyvalent alcohols, thus forming "external" ester groups, and in the partial esters of both these ester groups the non-esterified carboxy functions may be free or salified with metals or organic bases.

DETAILED DESCRIPTION OF THE INVENTION

Esterification between different polysaccharide molecules consequently increases their molecular weight, which can be roughly doubled or multiplied according to the number of molecules involved in the crosslinking. The degree of "polymerization" varies according to the conditions used in the preparation procedure described hereafter, such as temperature, reaction duration, but it may likewise depend on the polysaccharide to be crosslinked. Even though it is impossible to ascertain the ratio between the two types of ester bonds, an approximate representation can be made on the basis of the molecular weight, this being proportional to the number of molecules of the polysaccharide aggregate of the abovesaid bonds of intermolecular inner esters. Particularly important are the crosslinked products of the present invention, resulting from the fusion of two or three polysaccharide molecules, and products varying in their degree of "polymerization" in these terms. They can be obtained for example by means of the procedure used in the illustrative Examples.

The invention also concerns the use of the new inner esters, for example in the field of biodegradable plastic materials, to manufacture sanitary and surgical articles, in the cosmetic and pharmaceutical fields, in the food industry and in many other industrial fields.

Acid polysaccharides containing carboxy functions which serve as the basic starting materials to the new inner esters of the present invention are all those already known and described in literature, such as the natural ones of animal or vegetable origin, and synthetic derivatives of the same, but above all hyaluronic acid, alginic acid, carboxymethylcellulose, carboxymethyl starch (also referred to as "carboxymethylamide") and carboxymethylchitin. Also the external partial esters of acidic polysaccharides, such as those of hyaluronic acid and alginic acid, may serve as starting compounds. The partial esters of carboxymethylcellulose, of carboxymethylamide and carboxymethylchitin which can be used as starting materials are described in co-pending U.S. application Ser. No. 350,920, entitled "New Polysaccharide Esters", which is hereby incorporated by reference, was filed on the same day as the present application and is based upon Italian patent application No. 47963A/88. These partial esters can also be obtained according to the general preparation procedure for carboxy polysaccharide esters described in the European patent application No. 86305233.8 (Pub. No. 0216453, published on Apr. 1, 1987). As starting material it is also possible to use molecular fractions of the abovesaid acidic polysaccharides as well as their partial esters.

The specific use of the new esters can be determined and depends upon the overall degree of esterification, inner and possibly external, that is the number of esterified carboxy functions, and also the number of salified groups, as well as the degree of aggregation ("polymerization") of the molecules involved in the process of esterification. These indeed are the factors which determine the solubility of the product and its viscous-elastic properties. Thus, for example, the total esters are practically insoluble in aqueous liquids and are suitable, due to their molecular structure, for use in the manufacture of plastic materials and as additives for such materials. The esters with medium or low degrees of esterification and their salts with inorganic or organic bases are more or less soluble in aqueous conditions and are suitable for the preparation of gels destined for various uses, in the cosmetic and pharmaceutical fields and in the medical-sanitary field in general.

The autocross-linked products of the present invention may possess all the carboxy functions in the form of an inner ester, or only an aliquot part of the same. In these partial inner esters the percentage of "cross-links" varies preferably between 1 and 60%, and especially between 5 and 30% of the number of carboxy groups in the acidic polysaccharides.

The new inner esters of the present invention have become available because of the discovery of an original chemical procedure which is based on the activation of the carboxy groups by the addition of substances capable of inducing such activation. The unstable intermediate products obtained from the activation reaction separate spontaneously, either after the addition of catalysts and/or following a rise in temperature, forming the above mentioned inner ester bonds with hydroxyls of the same or other polysaccharide molecule. According to the degree of inner esterification desired, either all or an aliquot part of the carboxy functions are activated (the aliquot part being obtained by using an excess of activating substances or by suitable dosing methods).

The carboxy groups to be converted into inner ester groups can be activated starting from polysaccharides containing free carboxy groups, or, preferably, from polysaccharides containing salified carboxy groups, for example metal salts, preferably alkaline or alkaline earth metals, and above all with quaternary amonium salts, such as those descried hereafter. Salts with organic bases such as amines can however also be used as starting substances.

Methods for the activation of free or salified carboxy groups are per se known, particularly in the field of peptide synthesis, and those skilled in the art can easily determine which method is the most suitable, especially whether or not to use the starting substances in their free or salified form. Activation methods per se known for peptide synthesis procedures and useful in the preparation procedures of the present invention are described, for example, in Bodanszky, M., In search of new methods in peptide synthesis, Int. J. Peptide Protein Res. 25, 1985, 449–474; and Gross, E. et al., The Peptides, Analysis Synthesis, Biology, Academic Press, Inc., 1979, Vol. 1, Chapter 2. According to such procedures, a carboxyl component is activated, that is, a carboxyl component is converted to a reactive form. Such activation typically involves a reaction between an acid and an activating agent according to the scheme:

wherein X is an electron withdrawing moiety. Most activated derivatives of carboxylic acids, therefore, are mixed anhydrides, including in the broad sense also acid azides and acid chlorides which can be considered mixed anhydrides of hydrazoic acid and HCl as the activating agents. In addition, activation of a carboxyl component can be accomplished by the formation of intermediate "activated esters". These "activated esters" can be of various types, but particularly useful "activated esters" are those prepared by use of dicyclohexylcarbodiimide, p-nitrophenyl esters, trichlorophenyl esters, pentachlorophenyl esters, and O-acyl derivatives of hydroxylamines, particularly esters of N-hydroxysuccinimide.

All of these various types of activation procedures are useful in the preparation of the cross-linked carboxy polysaccharides of the invention, as all of these procedures can be characterized as importantly involving the reaction of a carboxyl group with an activating agent which essentially results in the formation of a substituent group that is easily reactive with a hydroxyl group so as to easily form the inner ester bonding characteristic of the products of the invention. The number of carboxy functions to be converted into inner esters is in proportion to the number of activated carboxy functions and this number depends on the quality of the activating agent used. In order to obtain total inner esters therefore, an excess of activating agents should be used, while in the case of partial esters, the quantity of this agent should be dosed according to the degree of esterification desired.

The carboxy groups which are still free or salified after the cross-linking reaction according to the present invention can be exchanged in order to obtain opportune salts or can be esterified with the abovementioned monovalent or polyvalent alcohols thus obtaining mixed esters, partly cross-linked and partly externally esterified. Of course, partial esterification with alcohols can be effected before activation of part of the carboxy groups and subsequent conversion into inner esters, that is, the abovementioned polysaccharide esters can be used as starting substances.

The new procedure for the preparation of cross-linked polysaccharides is therefore characterized by treating a polysaccharide, having free or salified carboxy groups and possibly also carboxy groups esterified with mono- or polyvalent alcohols, with an agent which activates the carboxy function, possibly in the presence of an auxiliary agent favouring the formation of intermediate activated derivatives and/or a tertiary organic or inorganic base, exposing the mixture to heating or irradiation (particularly with UV light) and, if desired, esterification with mono- or polyvalent alcohols of the carboxy groups still free or salified in the polysaccharides thus obtained, and if desired, by salifying free carboxy groups or by freeing salified carboxy groups. Of the substances able to activate the carboxy group, the conventional ones described in literature can be used, for example those usually used in the synthesis of peptides, except however those which would have the effect of altering or destroying the molecular structure of the starting polysaccharide, such as those used for the formation of carboxyl halides. Preferred substances which lead to the formation of activated esters are those, such as, carbodiimides, dicyclohexylcarbodiimide, benzyl-isopropyl-carbodiimmide, benzyl-ethyl-carbodiimmide; ethoxyacetylene; Woodward's reagent (N-ethyl-5-phenylisoxazolium-3'-sulfonate), or halogen derivatives from aliphatic, cycloaliphatic or aromatic hydrocarbons, or from heterocyclic compounds with halogen made mobile by the presence of one or more activating groups, such as chloroacetonitryl and especially the salts of 2-chloro-N-alkypyridine, such as chloride of 2-chloro-N-methyl-pyridine or other alkyl derivatives with inferior alkyl groups, such as those with up to 6 carbon atoms. In the place of chloride derivatives, other halogen derivatives can of course be used, such as bromide derivatives.

This activation reaction can be carried out in organic solvents, especially aprotic solvents such as dialkylsulfoxides, dialkylcarboxylamides, such as in particular lower alkyl dialkylsulfoxides, particularly dimethylsulfoxide, polymethylene sulfoxides, such as tetramethylene sulfoxide, dialkyls or polymethylene sulfones, such as tetramethylene sulfone, sulfolane and lower alkyl dialkylamides of lower aliphatic acids in which the alkyl groups have a maximum of six carbon atoms, such as dimethyl or diethyl formamide or dimethyl or diethyl acetamide. Other solvents may also be used, however, and these need not always be aprotic, such as alcohols, ethers, ketones, esters, such as lower aliphatic dialkyloxyhydrocarbides, such as dimethoxyethane and especially aliphatic or heterocyclic alcohols and ketones with a low boiling point, such as lower N-alkyl-pyrrolidones, such as N-methylpyrrolidone or N-ethyl-pyrrolidone, hexafluoroisopropanol and trifluoroethanol. If halogen derivatives are used as carboxyl-activating substances, especially in the form of salts, such as the above mentioned 2-chloro-N-methylpyridinium chloride, it is better to use a metal salt or a salt of the organic base of the starting polysaccharide, especially one of the quaternary ammonium salts described hereafter, such as tetrabutyl ammonium salt. These salts have the special advantage of being very soluble in the abovesaid organic solvents in which the crosslinking reaction is best effected, thus guaranteeing an excellent yield. It is advisable to add to the mixture a substance capable of subtracting acid, such as organic bases, carbonates, bicarbonates or alkaline or alkaline earth acetates, or organic bases and especially tertiary bases such as pyridine and its homologues, such as collidine, or aliphatic amine bases, such as triethylamine or N-methyl-piperazine.

The use of quaternary ammonium salts represents a particularly advantageous procedure of the present invention and constitutes one of its main objectives. Such ammonium salts are well known and are prepared in the same way as other known salts. They derive from alkyls having preferably between 1 and 6 carbon atoms. It is preferable to use tetrabutyl ammonium salts. One variation in the procedure of the present invention in which quaternary ammonium salts are used, consists in reacting an alkaline salt, for example sodium or potassium salt, in the presence of catalyzing quantity of a quaternary ammonium salt, such as tetrabutylammonium iodide.

The substances which catalyze activation of the carboxy groups to be added to the activating agents are reported in literature and these too are preferably bases such as those mentioned previously. Thus, for example, when the carboxy groups are activated with isothiazoline salts it is preferable to add some triethylamine to the reaction mixture.

The reaction of formation of activated intermediates, such as and especially esters, is carried out at the temperature recommended in literature and this temperature can however be varied should circumstances require as can be easily determined by one skilled in the art. The formation of inner ester bonds can come about within a fairly wide temperature range, for example between 0° C. and 150° C., preferably room temperature or slightly above, for example between 20° C. and 75° C. Raising the temperature favours the formation of inner ester bonds, as does exposure to radiations of suitable wavelength, such as ultraviolet rays.

In the produced polysaccharide crosslinked products, those remaining free carboxy groups or those in the form of salts can be partially or totally esterified with mono-or polyvalent alcohols, thus obtaining esters mixed with bonds which are in part internal and in part external. The alcohols used for this esterification correspond to those dealt with hereafter and from which the new mixed esters of the present invention are derived.

For esterification of the free or salified carboxy groups, known, conventional methods may be used, such as reaction between a carboxy salt, such as sodium salt, and an etherifying agent or the alcohols themselves in the presence of catalyzing substances, such as acid-type ion-exchangers. The known etherifying agents described in literature can be used, such as especially the esters of various inorganic acids or organic sulfonic acids, such as hydrogen acids, that is the hydrocarbyl halides such as methyl or ethyl iodide or neutral sulfates or hydrocarbyl acids, sulfites, carbonates, silicates, phosphites or hydrocarbyl sulphonates, such as methyl-, benzo-, or p-toluolsulfonate or methyl or ethyl chlorosulfonate. The reaction can take place in a suitable solvent, such as an alcohol, preferably the one corresponding to the alkyl group to be introduced into the carboxy group, but also nonpolar solvents such as ketones, ethers such as dioxane or aprotic solvents, such as dimethylsulfoxide. As a base, it is possible to use for example an alkaline or alkaline earth metal hydrate or magnesium or silver oxide or a basic salt of one of these metals, such as a carbonate and, of the organic bases, a tertiary nitrogenous base, such as pyridine or collidine. Instead of the base it is also possible to use a basic ion-exchanger. When starting from salts of partial polysaccharide esters, these may also be ammonium salts, such as ammonium or substituted ammonium salts.

According to one chemically original procedure described in the abovesaid European patent application No. 86305233.8, the external esters can be advantageously prepared by starting with quaternary ammonium salts with an etherifying agent in an aprotic solvent, such as dialkylsulfoxides, dialkylcarboxylamides, such as in particular lower alkyl dialkylsulfoxides with a maximum of 6 carbon atoms, particularly dimethylsulfoxide, and the lower alkyl dialkylamides of lower aliphatic acids, such as dimethyl or diethyl formamide or dimethyl or diethyl acetamide. Reaction should be effected preferably within a temperature range of between about 25° C. and 75° C. for example at about 30° C. Esterification is effected preferably by gradually adding the etherifying agent to the abovesaid ammonium salt dissolved in one of the solvents mentioned, for example in dimethylsulfoxide.

As alkylating agents it is possible to use those mentioned above, especially the alkyl halogens. As starting ammonium salts it is preferable to use lower ammonium tetraalkylates, since alkyl groups have preferably between 1 and 6 carbon atoms. It is best to use tetrabutyl ammonium salt. These quaternary ammonium salts can be prepared by reacting a metal salt of the acidic polysaccharide, in part internally esterified, preferably one of those mentioned above, especially sodium or potassium salt, in aqueous solution with a salified sulfonic resin with a quaternary ammonium base. The tetralkyl ammonium base of the polysaccharide ester can be obtained by freeze-drying the eluate. These starting salts are soluble in the above aprotic solvents, so that esterification according to this procedure is particularly easy and provides good yields. It is therefore only by following this procedure that the number of carboxy groups to be esterified can be exactly dosed.

One variation of this procedure consists in reacting potassium or sodium salt, suspended in a suitable solvent, such as dimethylsulfoxide, with a suitable alkylating agent in the presence of a catalyzing quantity of a quaternary ammonium salt, such as tetrabutyl ammonium iodide.

In the inner esters obtained according to the new procedure, the carboxy groups still left intact can be salified with organic or inorganic bases. The choice of bases for the formation of such salts is based on the intended use of the product. The inorganic salts are preferably those of alkaline metals, such as sodium or potassium salts or ammonium salts, cesium salts, salts of alkaline earth metals, such as calcium, magnesium or aluminum.

The salts of organic bases are especially those of aliphatic, araliphatic, cycloaliphatic or heterocyclic amines. The ammonium salts of this type may derive from therapeutically acceptable, but inactive, amines, or from amines with a therapeutic action. Of the former, special consideration should be given to aliphatic amines, for example, mono, di and trialkylamines, with alkyl groups with a maximum of 18 carbon atoms, or arylalkylamines with the same number of carbon atoms in the aliphatic part and where aryl means a benzene group possibly substituted by between 1 and 3 hydroxy groups. As therapeutically acceptable amines, but not active in themselves, cyclic amines are very suitable, such as alkylene amines with rings of between 4 and 6 carbon atoms, possibly interrupted in the ring by heteroatoms, such as oxygen, sulphur and nitrogen, such as piperidine, morpholine or piperazine, or may be substituted for example by amino or hydroxy functions, as in the case of aminoethanol, ethylene diamine or choline.

Should the crosslinked polysaccharides of the present invention be intended for pharmacological and therapeutic uses, their vehicling functions can be put to good use (as explained hereafter) for therapeutically active amines, preparing the salts of such amines. These salts can therefore derive from all basic nitrogenous drugs, such as those of the following groups: alkaloids, peptides, phenothiazines, benzodiazepines, thioxanthenes, hormones, vitamins, anticonvulsivants, antipsychotics, antiemetics, anesthetics, hypnotics, anorexigenics, tranquilizers, muscle relaxants, coronary vasodilators, antineoplastics, antibiotics, antibacterials, antivirals, antimalarials, carbonic anhydrase inhibitors, nonsteroid antiinflammatory agents, vasoconstrictors, cholinergic agonists, cholinergic antagonists, adrenergic agonists, adrenergic antagonists, narcotic antagonists.

The salts can be prepared in a manner per se known in the art, for example by treating the crosslinked polysaccharide having a certain number of free carboxy functions, with the calculated quantity of base. However, salts can also be formed by double exchange; for example it is possible to obtain alkaline salts, such as sodium salt, treating a solution of quaternary ammonium salt of the crosslinked polysaccharide and/or partially esterified, with an aqueous solution of alkaline chloride, and isolating the alkaline salt present, for example by precipitation with a suitable solvent, such as a ketone, for example with acetone.

The cross-linked polysaccharides of the present invention may use, as starting substrate, any natural or synthetic polysaccharide substituted by carboxy groups, such as those corresponding to the above starting materials for the procedure of the invention. The invention especially concerns cross-linked acidic polysaccharides derived from hyaluronic acid, from alginic acid, from carboxymethylcellulose, from carboxymethylamide and from carboxymethylchitin.

Hyaluronic acid derivatives are of major importance compared to derivatives of other series, due to the biological origin of the starting substrate, which permits the new crosslinked substances to be used in pharmaceutics, surgery and medicine in general.

The substrate of hyaluronic acid can be of any origin, such as acids extracted from the above natural starting materials, for example from cocks' combs. The preparation of these acids is described in literature: preferably, purified hyaluronic acids should be used. According to the invention, it is preferable to use hyaluronic acids constituting molecular fractions of the integral acids obtained directly by extraction of organic materials with a wide range of molecular weights, for example between 90%–80% and 0.2% of the molecular weight of the integral acid, preferably between 5% and 0.2%. These fractions can be obtained by various procedures described in literature, and that is with hydrolyzing, oxidizing or enzymatic chemical agents or physical procedures, for example mechanical or irradiation procedures, and often during the same purification procedures, primordial extracts may be formed. Separation and purification of the molecular fractions obtained comes about by means of known techniques, such as by molecular filtration. One purified HY fraction suitable to be used according to the invention is for example the one known as "noninflammatory-NIF-NaHA sodium hyaluronate", described by Balazs in the pamphlet "Healon"—A guide to its use in Ophthalmic Surgery—D. Miller & R. Stegmann, eds. John Wiley & Sons N.Y. 81983: p.5.

Also particularly important as starting materials for the esters of the present invention are two purified fractions which can be obtained from hyaluronic acid, for example the one extracted from cocks' combs, known by the names of "Hyalastine" and "Hyalectin". The fraction Hyalastine has an average molecular weight of about 50,000 to 100,000 while the fraction Hyalectin has an average molecular weight of about 500,000 to 730,000. One combined fraction of these two fractions has also been isolated and characterized as having an average molecular weight of between about 250,000 and about 350,000. This combined fraction can be obtained with a yield of 80% of the total hyaluronic acid available in the particular starting material, while the fraction Hyalectin can be obtained with a yield of 30% and the fraction Hyalastine with a yield of 50% of the starting HY. The preparation of these fractions is described in the above-mentioned European patent publication No. 0138572A3.

The alginic acid to be used to prepare new derivatives may be obtained by extraction from various natural materials, especially from brown algae (Phaecophyceae). The polysaccharide is constituted by chains of D-mannuronic acid and L-guluronic acid. The molecular weight is very varied, depending on its origin and can be, for instance, between 30,000 and 200,000. It depends not only on the type of alga used, but also on the season in which it was gathered, on the origin and age of the plant. The main species of brown algae used to obtain alginic acid are for example *Macrocystis pyrifera, Laminaria Cloustoni, Laminaria hyperborea, Laminaria Flexicaulis, Laminaria digitata, Ascophyllum nodosum* and *Fucus serratus*. Alginic acid is found in these algae as a diffuse component of the cell walls in the form of a mixture of its various alkaline salts, among which features especially sodium salt, a mixture known also as algin. These salts are normally extracted in aqueous conditions with a solution of sodium carbonate and from this extract alginic acid can be obtained directly by precipitation with an acid, for example a mineral acid such as hydrochloric acid, or indirectly by first making insoluble calcium salt.

Alginic acid or alkaline alginates can however by obtained by microbiological methods, for example by fermentation with *Pseudomonas aeruginosa* or *Pseudomonas putida, Pseudomonas fluorescens* or *Pseudomonas mendocina* mutants. Preparation of the various types of alginic acid is described in literature. For the purposes of the present invention, purified alginic acids should be used.

Carboxymethyl-derivatives of cellulose, starch and chitin are also useful in the present invention and have also been amply described in literature. Apart from carboxy polysaccharides themselves, it is possible to use their partial esters with mono or polyvalent alcohols as starting materials for the preparation of the new cross-linked products of the invention.

In the cross-linked polysaccharides of the invention which also have carboxy functions esterified with monovalent or polyvalent alcohols, whether these functions be present in the starting materials of the above mentioned procedure, or whether they be introduced at the end of the procedure, the alcohols may belong to the aliphatic, araliphatic, alicyclic or heterocyclic series.

The following description concerns the overall view of the above useful alcohols, on the understanding that the various groups and single compounds should be chosen on the basis of the particular polysaccharide substrates and their uses, as illustrated below. Thus, for example, one skilled in the art will know which alcohols are to be chosen for the cross-linked products intended for therapeutic and sanitary uses and which others are more suitable for the cross-linked products for use in the alimentary field or in the perfume industry or in the fields of resins and textiles.

Alcohols of the aliphatic series for use as esterifying components are for example those with a maximum of 34 carbon atoms, which can be saturated or unsaturated and which can possibly also be substituted by other free functional or functionally modified groups, such as amino, hydroxyl, aldehydo, keto, mercapto, carboxy groups or by groups deriving from these, such as hydrocarbyl or dihydrocarbylamino groups (here and hereafter meaning by the term "hydrocarbyl" not only monovalent radicals of carbohydrates for example type $C_nH_{2n+1}$, but also bivalent or trivalent radicals, such as "alkylenes" $C_nH_{2n}$ or "alkylidenes" $C_nH_{2n}$), ether or ester groups, acetal or ketal groups, thioether or thioester groups, and esterified carboxy groups or carbamidic and substituted carbamidic groups by one or two hydrocarbyl groups, by nitrile groups or halogens. Of the above groups containing hydrocarbyl radicals, these should preferably be inferior aliphatic radicals, such as alkylic, with a maximum of 6 carbon atoms. Such alcohols may then be interupted in the carbon atom chain by heteroatoms, such as atoms of oxygen, nitrogen and sulfur.

It is preferable to choose alcohols substituted with one or two of the abovesaid functional groups. Alcohols of the above group to be preferred for the purposes of the present invention are those with a maximum of 12 and especially 6 carbon atoms and in which the hydrocarbyl radicals in the abovesaid amino, ether, ester, thioether, thioester, acetal, ketal groups represent alkyl groups with a maximum of 4 carbon atoms, and also in the esterified carboxy groups or substituted carbamidic groups or hydrocarbyl groups are alkyls with the same number of carbon atoms, and in which the amino or carbamidic groups may be alkylene amine or alkylene carbamidic groups with a maximum of 8 carbon atoms. Of these alcohols special mention should be given to those which are saturated and unsubstituted such as methyl, ethyl, propyl, isopropyl alcohols, n-butyl alcohol, isobutyl alcohol, tert-butyl alcohol, amyl alcohols, pentyl, hexyl, octyl, nonyl and dodecyl alcohols and above all those with a linear chain, such as n-octyl and n-dodecyl alcohols. Of the substituted alcohols of this group, the following should be mentioned: bivalent alcohols such as ethylene glycol, propylene glycol, butylene glycol, trivalent alcohols such as glycerin, aldehyde alcohols such as tartronic alcohol, carboxy alcohols such as lactic acids, for example glycolic acid, malic acid, tartaric acids, citric acid, aminoalcohols, such as aminoethanol, aminopropanol, n-aminopropanol, n-aminobutanol and their dimethyl and diethyl derivatives in the amine function, choline, pyrrolidinylethanol, piperidinylethanol, piperazinylethanol and the corresponding derivatives of n-propyl or n-butyl alcohols, monothioethyleneglycol and its alkyl derivatives, for example the ethyl derivative in the mercapto function.

Of the higher aliphatic saturated alcohols, the following should be given as examples: cetyl alcohol and myricyl alcohol, but of special importance for the purposes of the present invention are the higher unsaturated alcohols with one or two double bonds, such as especially those contained in many essential oils and having affinity with terpenes, such as citronellol, geraniol, nerol, nerolidol, linalool, farnesol, phytol. Of the lower unsaturated alcohols, the ones to be considered are allyl alcohol and propargyl alcohol.

Of the araliphatic alcohols, special mention should be given to those with only one benzene residue and in which the aliphatic chain has a maximum of 4 carbon atoms and in which the benzene residue may be substituted by between 1 and 3 methyl or hydroxy groups or by halogen atoms, especially by chlorine, bromine, iodine, and in which the aliphatic chain may be substituted by one or more functions chosen from the groups comprising free amino groups or mono or dimethyl groups or by pyrrolidine or piperidine groups. Of these alcohols special mention should be given to benzyl alcohol and phenethyl alcohol.

Alcohols of the cycloaliphatic or aliphatic cycloaliphatic series may derive from mono or polycyclic carbohydrates, may preferably have a maximum of 34 carbon atoms, may be unsubstituted and may contain one or more substituents, such as those mentioned above for the aliphatic alcohols. Of the alcohols derived from single-ringed cyclic carbohydrates, special mention should be given to those with a maximum of 12 carbon atoms, the rings having preferably between 5 and 7 carbon atoms, which may be substituted for example by between one and three lower alkyl groups, such as methyl, ethyl, propyl, or isopropyl groups. As alcohols specific to this group, cyclohexanol, cyclohexanediol, 1,2,3 cyclohexanetriol and 1,3,5 cyclohexanetriol (phloroglucitol), inositol, should be mentioned, as well as the alcohols deriving from p-menthane, such as carvomenthol, menthol, α and γ-terpineol, 1-terpineol, 4-terpinenol and piperitol, or the mixture of these alcohols as "terpineol", 1,4- and 1,8-terpin. Of the alcohols deriving from carbohydrates with condensed rings, for example those of the thujane, pinane or camphane group, useful also are thujanol, sabinol, pinol hydrate, D and L-borneol and D and L-isoborneol.

Aliphatic-cycloaliphatic polycyclic alcohols to be used for the esters of the present invention are sterols, cholic acids and steroids, such as the sexual hormones and their synthetic analogues, and in particular corticosteroids and their derivatives. Thus it is possible to use for example: cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin and their alkyl derivatives, as well as the ethynyl or propynyl derivatives in position 17, for example 17-α-ethynyl-estradiol or 7-α-methyl-17-α-ethynyl-estradiol, pregnenolone, pregnanediol, testosterone and its derivatives, such as 17-α-methyltestosterone, 1,2-dehydrotestosterone and 17-α-methyl-1,2-dehydrotestosterone, alkynyl derivatives in position 17 of testosterone and 1,2-dehydrotestosterone, such as 17-α-ethynyltestosterone, 17-α-propynyltestosterone, norgestrel, hydroxyprogesterone, corticosterone, deoxycorticosterone, 19-nortestosterone, 19-nor-17-α-methyltestosterone and 19-nor-17-α-ethynyltestosterone, cortisone, hydrocortisone, prednisone, prednisolone, fludrocortisone, dexamethasone, betamethasone, paramethasone, flumethasone, fluocinolone, fluprednylidene, clobetasol, beclomethasone, aldosterone, desoxycorticosterone, alfaxalone, alfadolone, bolasterone.

Useful esterifying components for the esters of the present invention are genins, (aglycons) of cardioactive glycosides, such as digitoxigenin, gitoxigenin, digoxigenin, strophanthidin, tigogenin, saponins.

Other alcohols to be used according to the invention are vitamin alcohols such as axerophthol, vitamins $D_2$ and $D_3$, aneurine, lactoflavine, ascorbic acid, riboflavine, thiamine, pantothenic acid.

Heterocyclic alcohols may be considered to be derivatives of the abovesaid cycloaliphatic or aliphatic-cycloaliphatic alcohols, if their linear or cyclic chains are interrupted by one or more, for example between one and three ethero atoms chosen from the group formed by —O—, —S—, —N and —NH and in these there may be one or more unsaturated bonds for example double bonds, particularly between one and three, thus including also heterocyclic compounds with aromatic structures. The following are specific useful examples: furfuryl alcohol, alkaloids and derivatives such as atropine, scopolamine, cinchonine, cinchonidina, quinine, morphine, codeine, nalorphine, N-butylscopolammonium bromide, ajmaline; phenylethylamines such as ephedrine, isoproterenol, epinephrine; phenothiazine drugs such as perphenazine, pipothiazine, carphenazine, homofenazine, acetophenazine, fluphenazine, N-hydroxyethylpromethazine chloride; thioxanthene drugs such as flupenthizol and clopenthixol; anticonvulsivants such as meprophendiol, antipsychotics such as opipramol; antiemetics such as oxypendil; analgesics such as carbetidine and phenoperidine and methadol; hypnotics such as etodroxizine; anorexics such as benzhydrol and diphemethoxidine; mild tranquilizers such as hydroxyzine; muscle relaxants such as cinnamedrine, diphylline, mephenesin, methocarbamol, chlorphenesin, 2,2-diethyl-1,3-propanediol, guaifenesin, idrocilamide; coronary vasodilators such as dipyridamole and oxyfedrine; adrenergic blockers such as propanolol, timolol, pindolot, bupranolol, atenolol, metoprolol, practolol; antineoplastics such as 6-azauridine, cytarabine, floxuridine; antibiotics such as chloramphenicol, thiamphenicol, erythromycin, oleandomycin, lincomycin; antivirals such as idoxuridine; peripheral vasodilators such as isonicotinyl alcohol; carbonic anhydrase inhibitors such as sulocarbilate; antiasthmatics and antiinflammatories such as tiaramide; sulfamides such as 2-p-sulfanylanilinoethanol. While "inner" cross-linking of acid polysaccharides alone, without "external" esterification of the carboxy groups with alcohols of the aforesaid series, yields products which present properties similar to those of the starting products, but with the advantages mentioned previously, and may therefore be applied in all the fields in which the latter are used; simultaneous "external" esterification of the carboxy groups may prove useful in imparting to the polysaccharide properties specific to the alcohols themselves. In this case the crosslinked products act as a vehicle for the properties of the alcohols and in this manner can be put to good use in the pharmaceutical and medical fields. Thus, it is possible to prepare drugs containing cross-linked products according to the invention and therapeutically active alcohols, such as those listed above. Medicaments of this kind mainly have a hyaluronic acid base but those based on the other polysaccharides mentioned can also be used.

Salification, too, can have a double purpose, both in the manufacture of products in which the intrinsic properties of the basic polysaccharides are put to use, and in imparting to these the properties of the salifying bases, for example those with therapeutically active bases, for example those mentioned above.

The vehicling of a drug with the new cross-linked products can however also be achieved by the simple addition (physical mixture) of a drug and/or of a therapeutically active base to the polysaccharide. The present invention therefore also includes medicaments containing:

1. a pharmacologically active substance or an association of pharmacologically active substances and
2. a carrying vehicle comprising a cross-linked product of an acidic polysaccharide according to the invention Salts may be present in mixtures of this kind, should the following be chosen as component:

1) an organic base. Particularly important are associations of this type in which the component
2) is a cross-linked product having as its base hyaluronic acid or one of its esters.

The abovesaid medicaments may be in solid form, for example as freeze-dried powders containing only the two components 1) and 2) as a mixture or separately packed and this galenic form is especially suitable for topical use. Indeed such medicaments in solid form, on contact with the epithelium to be treated, form solutions which are more or less concentrated according to the nature of the particular epithelium and with the same characteristics as the solutions previously prepared in vitro and represent another aspect of the present invention. Such solutions are preferably in distilled water or in sterile physiological solutions and contain preferably no other pharmaceutical vehicle. The concentrations of these solutions may vary greatly, for example between 0.01 and 75%, both for the two separate components and for their mixtures. Preference should be given to solutions of a pronounced elastic viscous character, for example containing from 10% to 100% of the medicament or of each of the two components.

Particularly are medicaments of this type, both in an anhydrous form (freeze-dried powder) or as solutions, either concentrated or diluted in water or saline, possibly with the addition of additives or auxiliary substances, such as particularly disinfectants or mineral salts acting as buffer or others, for ophthalmic use, based on cross-linked hyaluronic acid.

Among the medicaments of the type described here, preference should be given, as the case may be, to those with a degree of acidity suitable to the area in which they are to be applied, that is, with a physiologically tolerable pH. The pH may be adjusted by suitably regulating the quantity of polysaccharide, of its salts and of any basic or acid substances which may be present.

The degree of cross-linking and esterification depends firstly on the properties which are to be obtained in the various fields of application, for example a lesser or greater degree of lipophilia or hydrophilia in cases of therapeutic application. Usually, a high degree of cross-linking and esterification increases the lipophilic character of a substance and therefore diminishes its solubility in water. For a therapeutic use of the new cross-linked products it is important to regulate the degree of esterification in order to ensure, despite good and improved lipophilia compared to the basic polysaccharides or their salts, a sufficient degree of hydrosolubility. Naturally, the molecular size of the esterifying components should be considered, as it usually influences hydrosolubility in an inversely proportional manner.

The new cross-linked products, esterified with therapeutically active alcohols and/or salified with therapeutically active bases or the abovesaid medicaments containing them, are therapeutically more efficacious, and have a greater and/or longer-lasting effect (retard effect) as compared to the starting drugs. Particularly important are medicaments of this type, based on polysaccharides which are highly compatible with the biological environment, such as in the case of hyaluronic acid.

Hyaluronic acid also constitutes however a very important substrate thanks to its own pharmaceutical action. The cross-linked products based on this polysaccharide, possibly also esterified with therapeutically inactive alcohols, have improved stability compared to hyaluronic acid itself and its esters. Such cross-linked products can be used for all known indications for the above compounds, for example hyaluronic acid itself, for example intraarticular injections with a lubricant action. As a result of the greater stability of the new cross-linked products with regard to hyaluronidase as compared to the free acid and to the esters, its action is greatly prolonged. The pharmacologically inert alcohols with which to esterify such cross-linked products of hyaluronic acid are preferably lower aliphatic alcohols with a maximum of 8 carbon atoms, especially saturated monovalent alcohols, such as ethanol, propyl alcohol, isopropyl alcohol, and n-butyl alcohol or isobutyl alcohol.

The cross-linked products based on hyaluronic acid are very suitable for cosmetic uses. Of the esters of these cross-linked products, important are those deriving from therapeutically inactive alcohols, such as for example saturated or unsaturated aliphatic alcohols, for example unsubstituted alcohols of this kind with a straight or ramified chain, for example with between 1 and 8 carbon atoms, such as those mentioned above. Particularly interesting are also unsaturated alcohols, for example with one or more double bonds, such as vinyl or allyl alcohols and their condensed derivatives, or polyvalent alcohols, such as glycerine. Also useful are aliphatic alcohols, for example those derived from cyclopentane or cyclohexane and their derivatives substituted by lower alkyl groups, for example alkyls with between 1 and 4 carbon atoms, especially by methyl groups. Particularly interesting are also esters with cycloaliphatic and aliphatic-cycloaliphatic alcohols derived from terpenes, such as those mentioned above and from therapeutically active alcohols, and which are also useful in cosmetics.

Extremely important is the use of cross-linked products based on hyaluronic acid for the manufacture of sanitary and surgical items. The esters of these cross-linked products are preferably those mentioned above for use in cosmetics.

The use of hyaluronic cross-linked products as vehicles for drugs intended for topical use is particularly useful in ophthalmology, where a particular compatibility is noted between the new products and the corneal epithelium, and therefore also excellent tolerability, with no sensitization effects. Furthermore, when the medicaments are administered in the form of concentrated solutions with elastic-viscous characteristics or in solid form, it is possible to obtain, on the corneal epithelium, homogenous and stable films which are perfectly transparent and adhering, which guarantee prolonged bioavailability of the drug and which therefore constitute excellent preparations with a retard effect. Such ophthalmic medicaments are particularly valuable in the veterinary field, considering that no chemotherapeutic specialities exist in this field, for example, veterinary specialities for ocular use containing chemotherapeutic components. As a result, preparations intended for humans are normally used and these do not always guarantee a specific range of action, nor they do allow for the particular conditions in which the treatment must be effected. This, for example, is the case of infective keratoconjunctivitis, pink eye or IBK, an infection which mainly affects cattle, sheep and goats.

The new cross-linked hyaluronic products and possibly medicaments of the type described above which contain them as component 2) may be applied in other fields too, and markedly in dermatology and in diseases of the mucosa, for example of the mouth. Furthermore, they can be used to obtain a systemic effect thanks to transuctaneous absorption, for example in suppositories. All these applications are possible both in human and veterinary medicine. In human medicine the new medicaments are particularly suitable for pediatric use. The present invention includes in particular any one of these therapeutic applications.

Also objects of the present invention are pharmaceutical preparations containing one or more cross-linked acidic polysaccharide products as defined above or associative medicaments containing them as component 2) also mentioned above. Apart from the therapeutically active substance or substances, such pharmaceutical preparations also contain the usual excipients and may be destined for oral, rectal, parenteral, subcutaneous, local or intradermal use. They are therefore in solid or semisolid form, for example pills, tablets, gelatinous capsules, capsules, suppositories, soft gelatin capsules. For parenteral and subcutaneous uses those forms intended for intramuscular or intradermal uses, or suitable for infusions or intravenous injections can be used, and can therefore be presented as solutions of the active compounds or as freeze-dried powders of the active compounds to be mixed with one or more pharmaceutically acceptable excipients or diluents, and which are suitable for the above uses being osmotically compatible with the physiological fluids. For local use, those preparations in the form of sprays should be considered, for example nasal sprays, creams and ointments for topical use or sticking plasters specially prepared for intradermal administration. Solubility of the cross-linked products in organic solvents with low boiling points makes them particularly suitable for the manufacture of "sprays".

The preparations of this invention can be administered to man or animal. They contain preferably between 0.01% and 10% of active component for the solutions, sprays, ointments and creams and between 1% and 100% and preferably between 15% and 50% of active compound for the solid form preparations. Dosages to be administered will depend on individual diagnoses, on the desired effect and on the chosen administration route. The daily dosages of these preparations can be deducted from those already used both for the basic polysaccharide (as in the case of hyaluronic acid) for the corresponding cures, for example the cure for arthritis, for example in man or horse, and for the alcoholic component, in the case of esters, or of component 1) in the above medicaments, should these components represent the active principal whose action is to be exploited. Thus, for example, a cross-linked product of hyaluronic acid esterified even partially with cortisone, can be dosed according to its content of this steroid and to the usual dosage of the same in the known pharmaceutical preparations.

The preparation of salts according to the invention can be carried out in per se known procedures, by bringing into contact solutions either in aqueous suspensions or in organic solvents of the two components 1) and 2) and possibly of bases or basic salts of the above alkaline or alkaline earth metals or magnesium or aluminium in calculated quantities and isolating the salts in amorphous anhydrous form according to known techniques. It is possible for example to first prepare aqueous solutions of the two components 1) and 2), release such components from aqueous solutions of their salts with suitable ionic exchangers, mix the two solutions at a low temperature, for example between 0° C. and 20° C., if the salt thus obtained is easily soluble in water it can be freeze-dried, while poorly soluble salts may be separated by centrifugation or filtration or decantation and possibly subsequently dried.

For these associated medicaments too, dosage is based on that of the active principles used singly and may therefore be easily determined by one skilled in the art, taking into consideration the dosages recommended for corresponding known drugs. In the cosmetic articles according to the invention, the cross-linked acidic polysaccharide products and their salts are mixed with the excipients commonly used in the art and are for example those already listed above for pharmaceutical preparations. Above all, creams, ointments, lotions for topical use are used, in which the crosslinked polysaccharide or one of its salts can constitute the active cosmetic principle, possibly with the addition of other cosmetically active principles, such as for example steroids, for example pregnenolone, or one of the principles already reported. In such polysaccharides, the carboxy groups not used in cross-linking are preferably free or salified or are esterified with pharmacologically inactive alcohols, for example one of the lower aliphatic alcohols mentioned previously. The cosmetic articles can however also contain groups esterified with alcohols which have themselves a cosmetic action or an action which is auxiliary to the same, such as for example disinfectant substances, sunshields, waterproofing or regenerating or antiwrinkle substances or odoriferous substances, especially perfumes. Such substances may however also be simply mixed with the cross-linked polysaccharide, thus constituting cosmetic compositions similar to the medicaments previously described in which the pharmaceutically active component 1) is substituted by a cosmetological factor. Use of the cosmetic preparations of the present invention in the perfume industry represents a great step forward in techniques, since it allows slow, constant and protracted release of the odorous principles.

An important object of the present invention is constituted by sanitary and surgical articles, by their manufacturing methods and by their use. These articles are for example similar to those already known and commercially available or described in literature, for example those with a hyaluronic acid base, for example inserts or ophthalmic lenses.

Surgical and sanitary articles of special importance are those which can be obtained from appropriate solutions of the cross-linked products in organic liquids which are capable of being made into films, sheets and threads to be used in surgery as auxiliary or substitutive articles for the skin in cases of serious damage to this organ, such as burns, or as suture threads in surgery. The invention includes particularly these uses and a preparation procedure for these articles consisting in (a) forming a solution of the crosslinked polysaccharide or of one of its salts in an organic solvent; (b) making this solution into sheet or thread form; and (c) removing the organic solvent.

The formation of a solution of the crosslinked polysaccharide or of one of its salts is conducted in a suitable organic solvent, for example a ketone, an ester or an aprotic solvent such as an amide of a carboxy acid, especially a dialkylamide or of an aliphatic acid with between 1 and 5 carbon atoms and deriving from alkyl groups with between 1 and 6 carbon atoms, and above all from an organic sulfoxide, that is a dialkylsulfoxide with alkyl groups with a maximum of 6 carbon atoms, such as especially dimethylsulfoxide or diethylsulfoxide and also especially a fluorurate solvent with a low boiling point, such as especially hexafluoro-isopropanol.

Removing the organic solvent (c) is conducted by contact with another organic or aqueous solvent which must be mixable with the first solvent and in which the polysaccharide ester is insoluble, especially a lower aliphatic alcohol, for example ethyl alcohol (wet spinning), or, should a solvent with a not too high boiling point be used to prepare the solution of the polysaccharide derivative, in removing this same solvent by dry spinning, that is with a gas current and especially with suitably heated nitrogen. Dry-wet spinning can also be used with excellent results.

Particularly important are threads obtained with cross-linked products with a hyaluronic acid base, which can be used for the preparation of lints for the medication of wounds and in surgery. The use of such lints has the special advantage of being biodegradable to hyaluronic acid in the organism, by means of naturally existing enzymes. If cross-linked products containing also ester groups are used, these should be chosen from among those deriving from therapeutically acceptable alcohols, so that after enzymatic scission, apart from hyaluronic acid, innocuous alcohols are also formed, such as ethyl alcohol.

In the preparation of the abovesaid sanitary and surgical articles, it is possible also to include to advantage plasticizing materials in order to improve their mechanical characteristics, such as in the case of threads, to improve their resistance to tangles. Such plasticizers may be for example alkaline salts of fatty acids, for example sodium stearate, esters of organic acids with a high number of carbon atoms and the like.

Another application of hyaluronic cross-linked products where their biodegradability by esterases present in the organism is exploited, is represented by the preparation of capsules for subcutaneous implantation of medicaments or microcapsules by injection, for example by subcutaneous or intramuscular route. Up till now, for the application of subcutaneous medicaments designed to give slow release and therefore a retard effect, capsules made of silicon materials have been used, with the disadvantage that such capsules tend to migrate within the organism with no possibility of recovering them. Clearly, with the new hyaluronic derivatives this danger has been eliminated.

Of great importance is the preparation of microcapsules based on cross-linked hyaluronic products, eliminating the problems associated with their use, until now very limited for the same reasons as those explained above and opening up a vast field of application wherever a retard effect by injective route is desired.

Another application in the fields of medicine and surgery of the cross-linked hyaluronic products is represented by the preparation of various solid inserts such as plates, discs, sheets, and the like to replace those currently in use which are made of metal or synthetic plastic material, wherever these inserts are destined for removal after a certain period of time. Preparations with an animal collagen base, being proteic by nature, often have unpleasant side effects such as inflammation or rejection. In the case of cross-linked hyaluronic products, even though they are made of animal and not human hyaluronic acid, this danger does not exist as there is no incompatibility between the polysaccharides of various animal species.

Another application regards their use in increasing and correcting defects in the soft tissues: for a long time now there has been an urgent call for safe and effective biomaterials with which to substitute lost or damaged soft tissues. Many materials have been used such as paraffin, teflon paste, silicone and bovine collagen to replace lost soft tissues. However, these materials were associated with undesirable and permanent changes in the skin, with in situ migration of implants and negative reactions. For this reason there is a constant call in medicine for a versatile biomaterial. The cross-linked products of hyaluronic acid may be safely used to correct such defects of the soft tissues such as acne scars, postsurgical atropic irregularities, Mobs' chemosurgery, lacerated scars of the lip and old-age wrinkles.

Part of the applications in the fields of medicine and surgery of the new hyaluronic derivatives according to the present invention are preparations made of expanding material, especially in the form of sponges, for the medication of wounds or various lesions.

The above applications of the cross-linked products with a hyaluronic acid base represent the ideal solution for those sanitary and surgical articles which are intended to be introduced in one way or another into human or animal organisms or to be externally applied to the same. It is also possible however to make the same articles, using other cross-linked polysaccharides according to the invention, such as those mentioned above and especially those with an alginic acid base. In the same way, too, the cross-linked products are broken down in the organism to give basic polysaccharides which are generally well tolerated by the organism with no danger of rejection.

Of the cross-linked alginic acid products, special mention should be given to industrial and household uses and articles and alimentary articles and their uses. These, especially in the form of cross-linked partial salts, possibly further esterified with inert alcohols, such as especially lower aliphatic alcohols, for the preparation of gels, which can be widely used in the food industry, for the manufacture of ice-creams, puddings and many other kinds of sweet foods. Another property of these cross-linked products is their capacity for retaining water, because of which they can be used for example for the preservation of many frozen foods. A third property is their ability to emulsify and to stabilize emulsions. From this point of view, too, the alginic cross-linked products are important in the food industry, where they serve in the preparation of condiments and for the stabilization of many drinks such as beer and fruit juice, sauces and syrups. As emulsifiers, alginic cross-linked products can be used in the manufacture of polishes, anti-foam agents, lactics and as stabilizers in the ceramics and detergent industries. They can also be used in the paper industry, to make adhesive products, in textile printing and dyeing.

With regard to the physical, pharmacological and therapeutic properties, the substantial equivalence between the acidic polysaccharide cross-linked products of the present invention, possibly esterified with the abovesaid alcohols, and their salts, such as metal salts, it should be understood that the facts previously reported regarding the nonsalified products are true also of the salts.

The present invention also includes modifications in the preparation procedure for the new cross-linked products and their salts, in which a procedure is interrupted at any one stage or in which a procedure is begun with an intermediate compound and the remaining stages are carried out, or in which the starting products are formed in situ.

The invention is illustrated by the following illustrative examples, without these in any way limiting its scope.

EXAMPLE 1

Preparation of Cross-Linked Hyaluronic Acid (HY)
Product Description
  1% of carboxy groups used in internal esterification.
  99% of carboxy groups salified with sodium.

6.21 g of HY tetrabutylammonium salt with a molecular weight of 170,000 corresponding to 10 mEq of a monomeric unit are solubilized in 248 ml of DMSO at 25° C., 0.01 g (0.1 mEq) of triethylamine are added and the resulting solution is agitated for 30 minutes.

A solution of 0.026 g (0.1 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

3.97 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 2

Preparation of Cross-Linked Hyaluronic Acid (HY)
Product Description
  5% of carboxy groups used in internal esterification.
  95% of carboxy groups salified with sodium.

6.21 g of HY tetrabutylammonium salt with a molecular weight of 85,000 corresponding to 10 mEq of a monomeric unit are solubilized in 248 ml of DMSO at 25° C., 0.051 gr (0.5 mEq) of triethylamine are added and the resulting solution is agitated for 30 minutes.

A solution of 0.128 gr (0.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.95 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 3

Preparation of Cross-Linked Hyaluronic Acid (HY)
Product Description
  10% of carboxy groups used in internal esterification.
  90% of carboxy groups salified with sodium.

6.21 g of HY tetrabutylammonium salt with a molecular weight of 620,000 corresponding to 10 mEq of a monomeric unit are solubilized in 248 ml of DMSO at 25° C., 0.101 gr (1.0 mEq) of triethylamine is added and the resulting solution is agitated for 30 minutes.

A solution of 0.255 gr (1.0 mEq) of 2-chloro-1-methyl-pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.93 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 4

Preparation of Cross-Linked Hyaluronic Acid (HY)
Product Description
  25% of carboxy groups used in internal esterification.
  75% of carboxy groups salified with sodium.

6.21 g of HY tetrabutylammonium salt with a molecular weight of 170,000 corresponding to 10 mEq of a monomeric unit are solubilized in 248 ml of DMSO at 25° C., 0.253 g (2.5 mEq) of triethylamine are added and the resulting solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.85 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 5

Preparation of Cross-Linked Hyaluronic Acid (HY)
Product Description
  50% of carboxy groups used in internal esterification.
  50% of carboxy groups salified with sodium.

6.21 g of HY tetrabutylammonium salt with a molecular weight of 85,000 corresponding to 10 mEq of a monomeric unit are solubilized in 248 ml of DMSO at 25° C., 0.506 g (5.0 mEq) of triethylamine are added and the resulting solution is agitated for 30 minutes.

A solution of 1.28 gr (5 mEq) of 2-chloro-1-methylpyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30°.

3.65 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 6

Preparation of Cross-Linked Hyaluronic Acid (HY)
Product Description

75% of carboxy groups used in internal esterification. 25% of carboxy groups salified with sodium.

6.21 g of HY tetrabutylammonium salt with a molecular weight of 170,000 corresponding to 10 mEq of a monomeric unit are solubilized in 248 ml of DMSO at 25° C., 0.759 gr (7.5 mEq) of triethylamine is added and the resulting solution is agitated for 30 minutes.

A solution of 1.92 gr (7.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.54 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 7

Preparation of Cross-Linked Hyaluronic Acid (HY)
Product Description

100% of carboxy groups used in internal esterification.

6.21 g of HY tetrabutylammonium salt with a molecular weight of 70,000 corresponding to 10 mEq of a monomeric unit are solubilized in 248 ml of DMSO at 25° C., 1.012 gr (10 mEq) of triethylamine are added and the resulting solution is agitated for 30 minutes.

A solution of 2.55 gr (10 mEq) of 2-chloro-1-methyl pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is filtered and washed six times with 100 ml of acetone and lastly vacuum-dried for 24 hours at 30° C.

3.52 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 8

Preparation of the Partial Ethyl Ester of Cross-Linked Hyaluronic Acid (HY)
Product Description 25% of carboxy groups esterified with ethanol; 25% of carboxy groups used in internal esterification.

50% of carboxy groups salified with sodium.

6.21 g of HY tetrabutylammonium salt with a molecular weight of 170,000 corresponding to 10 mEq of a monomeric unit are solubilized in 248 ml of DMSO at 25° C., 0.390 gr (2.5 mEq) of ethyl iodide are added and the solution is kept for 12 hours at 30°. 0.253 gr (2.5 mEq) of triethylamine are added and the solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is slowly poured into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.84 grs of the title compound are obtained. Quantitative determination of the ethoxy groups is carried out according to the method of R. H. Cundiff and P. C. Markunas (Anal. Chem. 33, 1028–1930 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 9

Preparation of the Partial Ethyl Ester of Cross-Linked Hyaluronic Acid (HY)
Product Description 50% of carboxy groups esterified with ethanol; 25% of carboxy groups used in internal esterification. 25% of carboxy groups salified with sodium.

6.21 g of HY tetrabutylammonium salt with a molecular weight of 85,000 corresponding to 10 mEq of a monomeric unit are solubilized in 248 ml of DMSO at 25° C., 0.780 g (5.0 mEq) of ethyl iodide are added and the solution is kept for 12 hours at 30° C. 0.253 gr (2.5 mEq) of triethylamine are added and the solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.87 grs of the title compound are obtained. Quantitative determination of the ethoxy groups is carried out according to the method of R. H. Cundiff and P. C. Markunas (Anal. Chem. 33, 1028–1930 (1961). Quantitative determination of the total ester groups is carried out according to the saponi-

EXAMPLE 10

Preparation of the Ethyl Ester of Cross-Linked Hyaluronic Acid (HY)

Product Description

75% of carboxy groups esterified with ethanol; 25% of carboxy groups used in internal esterification.

6.21 g of HY tetrabutylammonium salt with a molecular weight of 170,000 corresponding to 10 mEq of a monomeric unit are solubilized in 248 ml of DMSO at 25° C., 1.17 gr (7.5 mEq) of ethyl iodide are added and the solution is kept for 12 hours at 30° C.

0.253 g (2.5 mEq) of triethylamine are added and the solution is agitated for 30 minutes.

A solution of 0.639 gr (2.5 mEq) of 2-chloro-1-methyl pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is filtered and washed five times with 100 ml of acetone and lastly vacuum-dried for 24 hours at 30° C.

3.91 grs of the title compound are obtained. Determination of the ethoxy groups is carried out according to the method of R. H. Cundiff and P. C. Markunas (Anal. Chem. 33, 1028–1930 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 11

Preparation of Cross-Linked Alginic Acid

Product Description

1% of carboxy groups used in internal esterification. 99% of carboxy groups salified with sodium.

4.17 g of alginic acid tetrabutylammonium salt (from alginic acid obtained from *Laminaria hyperborea*) corresponding to 10 mEq of a monomeric unit are solubilized in 248 ml of DMSO at 25° C., 0.010 gr (0.1 mEq) of triethylamine are added and the resulting solution is agitated for 30 minutes. A solution of 0.026 g (0.1 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

1.90 grs of the title compound are obtained. Quantitative determination of the total ester groups is carried out according to the saponification method described on pp 169–172 of "Quantitative Organic Analysis Via Functional Groups" 4th Edition John Wiley and Sons Publication.

EXAMPLE 12

Preparation of Cross-Linked Alginic Acid

Product Description

5% of carboxy groups used in internal esterification.
95% of carboxy groups salified with sodium.

4.17 g of alginic acid tetrabutylammonium salt (from alginic acid obtained from *Areophyllum modosum*) corresponding to 10 mEq of a monomeric unit are solubilized in 248 ml of DMSO at 25° C., 0.051 g (0.5 mEq) of triethylamine are added and the solution is agitated for 30 minutes.

A solution of 0.128 g (0.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

1.91 grs of the title compound are obtained. Quantitative determination of the total ester groups is carried out according to the saponification method described on pp 169–172 of "Quantitative Organic Analysis Via Functional Groups" 4th Edition John Wiley and Sons Publication.

EXAMPLE 13

Preparation of Cross-Linked Alginic Acid

Product Description

10% of carboxy groups used in internal esterification.
90% of carboxy groups salified with sodium.

4.17 gr of alginic acid tetrabutylammonium salt (from alginic acid obtained from *Macrocystis pyrifera*) corresponding to 10 mEq of a monomeric unit are solubilized in 248 ml of DMSO at 25° C., 0.101 g (0.5 mEq) of triethylamine are added and the resulting solution is agitated for 30 minutes.

A solution of 0.255 g (1.0 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

1.90 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 14

Preparation of Cross-Linked Alginic Acid

Product Description

25% of carboxy groups used in internal esterification.
75% of carboxy groups salified with sodium.

4.17 g of alginic acid tetrabutylammonium salt (from alginic acid obtained from *Laminaria hyperborea*) corresponding to 10 mEq of a monomeric unit are solubilized in 248 ml of DMSO at 25° C., 0.253 gr (2.5 mEq) of triethylamine are added and the resulting solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30°.

1.80 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 15

Preparation of Cross-Linked Alginic Acid
Product Description

50% of carboxy groups used in internal esterification.
50% of carboxy groups salified with sodium.

4.17 gr of alginic acid tetrabutylammonium salt (from alginic acid obtained from *Macrocystis pyrifera*) corresponding to 10 mEq of a monomeric unit are solubilized in 248 ml of DMSO at 25° C., 0.506 gr (5.0 mEq) of triethylamine are added and the resulting solution is agitated for 30 minutes.

A solution of 1.280 gr (5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and finally vacuum-dried for 24 hours 30° C.

1.72 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 16

Preparation of Cross-Linked Alginic Acid
Product Description

75% of carboxy groups used in internal esterification.
25% of carboxy groups salified with sodium. 4.17 gr of alginic acid tetrabutylammonium salt (from alginic acid obtained from *Areophyllum nodosum*) corresponding to 10 mEq of a monomeric unit are solubilized in 248 ml of DMSO at 25° C., 0.759 g (7.5 mEq) of triethylamine are added and the resulting solution is agitated for 30 minutes.

A solution of 1.932 g (7.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

1.59 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 17

Preparation of Cross-Linked Alginic Acid
Product Description

100% of carboxy groups used in internal esterification.

4.17 g of alginic acid tetrabutylammonium salt (from alginic acid obtained from *laminaria hyperborea*) corresponding to 10 mEq of a monomeric unit are solubilized in 248 ml of DMSO at 25° C., 1.012 g (10 mEq) of triethylamine are added and the resulting solution is agitated for 30 minutes.

A solution of 2.55 gr (10 mEq) of 2-chloro-1-methyl pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml of acetone and lastly vacuum-dried for 24 hours at 30° C.

1.52 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 18

Preparation of the Partial Ethyl Ester of Cross-Linked Alginic Acid
Product Description 25% of carboxy groups esterified with ethanol.
25% of carboxy groups used in internal esterification.
50% of carboxy groups salified with sodium.

4.17 gr of alginic acid tetrabutylammonium salt (from alginic acid obtained from *Areophyllum nodosum*) corresponding to 10 mEq of a monomeric unit are solubilized in 248 ml of DMSO at 25° C., 0.390 gr (2.5 mEq) of ethyl iodide are added and the solution is kept for 12 hours at 30° C. 0.253 gr (2.5 mEq) of triethylamine are added and the solution is agitated for 30 minutes.

A solution of 0.639 gr (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone while under constant agitation. A precipitate is formed which is then filtered and washed three times with 100 ml of acetone/water 5:1 and three times with 100 ml of acetone and lastly vacuum-dried for 24 hours at 30° C.

1.8 grs of the title compound are obtained. Quantitative determination of the ethoxy groups is carried out according to the method of R. H. Cundiff and P. C. Markunas (Anal. Chem. 33, 1028–1930 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 19

Preparation of the Partial Ethyl Ester of Cross-Linked Alginic Acid
Product Description 50% of carboxy groups esterified with ethanol.
25% of carboxy groups used in internal esterification.
25% of carboxy groups salified with sodium.

4.17 g of alginic acid terbutylammonium salt (from alginic acid obtained from *Laminaria hyperborea*) corresponding to 10 mEq of a monomeric unit are solubilized in 248 ml of DMSO at 25° C., 0.78 gr (5.0 mEq) of ethyl iodide are added and the solution is kept for 12 hours at 30° C. 0.253 g (2.5 mEq) of triethylamine are added and the solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

1.78 grs of the title compound are obtained. Quantitative determination of the ethoxy groups is carried out according to the method of R. H. Cundiff and P. C. Markunas (Anal. Chem. 33, 1028–1030 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 20

Preparation of the Ethyl Ester of Cross-Linked Alginic Acid
Product Description
75% of carboxy groups esterified with ethanol.
25% of carboxy groups used in internal esterification.

4.17 g of alginic acid tetrabutylammonium salt (from alginic acid obtained from *macrocystis pyrifera*) corresponding to 10 mEq of a monomeric unit are solubilized in 248 ml of DMSO at 25° C., 1.17 gr (7.5 mEq) of ethyl iodide are added and the solution is kept for 12 hours at 30° C. 0.253 gr (2.5 mEq) of triethylamine are added and the solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed three times with 100 ml of acetone and lastly vacuum-dried for 24 hours at 30° C.

1.86 grs of the title compound are obtained. Quantitative determination of the ethoxy groups is carried out according to the method of R. H. Cundiff and P. C. Markunas (Anal. Chem. 33, 1028–1030 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 21

Preparation of Cross-Linked Carboxymethylchitin
Product Description
1% of carboxy groups used in internal esterification.
99% of carboxy groups salified with sodium.

10 mEq. of sodium salt of a carboxylmethylchitin with a substitution rate of 0.99, prepared according to Trujillo (Carbohydrate Res. 7, 483 (1968), corresponding to 2.85 g of dry compound, are solubilized in 300 ml of distilled water. The solution is then passed through a thermostatic column regulated at 4° C. and containing 15 ml of sulfonic resin (Dowex 50 x 8) in the form of tetrabutylammonium.

5.05 gr of the tetrabutylammonium salt of a carboxymethylchitin with a 0.99 substitution ratio corresponding to 10 mEq of carboxy groups are solubilized in 248 ml of DMSO at 25° C., 0.01 g (0.1 mEq) of triethylamine are added and the resulting solution is agitated for 30 minutes.

A solution of 0.026 gr (0.1 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and finally vacuum dried for 24 hours at 30° C.

2.78 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 22

Preparation of Cross-Linked Carboxymethylchitin
Product Description
5% of carboxy groups used in internal esterification.
95% of carboxy groups salified with sodium.

5.05 g of the tetrabutylammonium salt of a carboxymethylchitin with a 0.99 substitution ratio corresponding to 10 mEq of carboxy groups are solubilized in 248 ml of DMSO at 25° C., 0.051 g (0.5 mEq) of triethylamine are added and the resulting solution is agitated for 30 minutes.

A solution of 0.128 g (0.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of ace-ghjne while kept under constant agitation. A precipitate is formed which is then filtered and washed three times with 100 ml of acetone/water 5:1 and three times with 100 ml of acetone and lastly vacuum-dried for 24 hours at 30° C.

2.74 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 23

Preparation of Cross-Linked Carboxymethylchitin
Product Description
10% of carboxy groups used in internal esterification.
90% of carboxy groups salified with sodium.

5.05 g of the tetrabutylammonium salt of a carboxymethylchitin with a 0.99 substitution ratio corresponding to 10 mEq of carboxy groups, are solubilized in 248 ml of DMSO at 25° C., 0.101 g (1.0 mEq) of triethylamine are added and the resulting solution is agitated for 30 minutes.

A solution of 0.255 g (1.0 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

2.73 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 24

Preparation of Cross-Linked Carboxymethylchitin
Product Description

25% of carboxy groups used in internal esterification.
75% of carboxy groups salified with sodium.

5.05 gr of the tetrabutylammonium salt of a carboxymethylchitin with a 0.99 substitution ratio corresponding to 10 mEq of carboxy groups, are solubilized in 248 ml of DMSO at 25° C. 0.253 gr (2.5 mEq) of triethylamine are added and the resulting solution is agitated for 30 minutes.

A solution of 0.639 gr (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

2.68 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 25

Preparation of Cross-Linked Carboxymethylchitin
Product Description

50% of carboxy groups used in internal esterification.
50% of carboxy groups salified with sodium.

5.05 g of the tetrabutylammonium salt of a carboxymethylchitin with a 0.99 substitution ratio corresponding to 10 mEq of carboxy groups, are solubilized in 248 ml of DMSO at 25° C. 0.506 gr (5.0 mEq) of triethylamine are added and the resulting solution is agitated for 30 minutes.

A solution of 1.28 gr (5.0 meq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

2.61 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 26

Preparation of Cross-Linked Carboxymethylchitin
Product Description

75% of carboxy groups used in internal esterification.
25% of carboxy groups salified with sodium.

5.05 g of the tetrabutylammonium salt of a carboxymethylchitin with a 0.99 substitution ratio corresponding to 10 mEq of carboxy groups, are solubilized in 248 ml of DMSO at 25° C. 0.759 gr (7.5 mEq) of triethylamine are added and the resulting solution is agitated for 30 minutes.

A solution of 1.932 gr (7.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

2.52 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 27

Preparation of Cross-Linked Carboxymethylchitin
Product Description

100% of carboxy groups used in internal esterification.

5.05 gr of the tetrabutylammonium salt of a carboxymethylchitin with a 0.99 substitution ratio corresponding to 10 mEq of carboxy groups, are solubilized in 248 ml of DMSO at 25° C. 1.01 gr (10 mEq) of triethylamine are added and the resulting solution is agitated for 30 minutes.

A solution of 2.55 gr (10 mEq) of 2-chloro-1-methyl pyridinium iodide (10 mEq) in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml of acetone and lastly vacuum-dried for 24 hours at 30° C.

2.42 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 28

Preparation of the Ethyl Ester of Cross-Linked Carboxymethylchitin
Product Description 25% of carboxy groups esterified with ethanol.
25% of carboxy groups used in internal esterification.
25% of carboxy groups salified with sodium.

5.05 gr of the tetrabutylammonium salt of a carboxymethylchitin with a 0.99 substitution ratio corresponding to 10 mEq of carboxy groups, are solubilized in 248 ml of DMSO at 25° C. 0.39 gr (2.50 mEq) of ethyl iodide are added and the solution is kept for 12 hours at 30° C. 0.253 gr (2.5 mEq) of triethylamine are added and the solution is agitated for 30 minutes.

A solution of 0.639 gr (2.5 mEq) of 2-chloro-1-methyl pyridinium iodide (10 mEq) in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone while under constant agitation.

The resulting mixture is slowly poured into 750 ml of acetone, maintaining continual agitation. A precipitate is formed which is then filtered and washed five times with 100 ml of acetone and lastly vacuum-dried for 24 hours at 30° C.

2.69 grs of the title compound are obtained. Quantitative determination of the ethoxy groups is carried out according to the method of R. H. Cundiff and P. C. Markunas (Anal. Chem. 33, 1028–1030 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 29

Preparation of the Ethyl Ester of Cross-Linked Carboxymethylchitin
Product Description 50% of carboxy groups esterified with ethanol. 25% of carboxy groups used in internal esterification.

25% of carboxy groups salified with sodium. 5.05 gr of the tetrabutylammonium salt of a carboxymethylchitin with a 0.99 substitution ratio corresponding to 10 mEq of carboxy groups, are solubilized in 248 ml of DMSO at 25° C. 0.78 gr (5.0 mEq) of ethyl iodide are added and the solution is kept for 12 hours at 30° C. 0.253 gr (2.5 mEq) of triethylamine are added and the solution is agitated for 30 minutes.

A solution of 0.639 gr (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone while under constant agitation. A precipitate is formed which is then filtered and washed five times with 100 ml of acetone and lastly vacuum-dried for 24 hours at 30° C. 2.71 grs of the title compound are obtained. Quantitative determination of the ethoxy groups is carried out according to the method of R. H. Cundiff and P. C. Markunas (Anal. Chem. 33, 1028–1030 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 30

Preparation of the Ethyl Ester of Cross-Linked Carboxymethylchitin
Product Description 75% of carboxy groups esterified with ethanol.

25% of carboxy groups used in internal esterification.

5.05 g of the tetrabutylammonium salt of a carboxymethylchitin with a 0.99 substitution ratio corresponding to 10 mEq of carboxy groups, are solubilized in 248 ml of DMSO at 25° C., 1.71 gr (7.5 mEq) of ethyl iodide are added and the solution is kept for 12 hours at 30° C. 0.253 gr (2.5 mEq) of triethylamine are added and the solution is agitated for 30 minutes.

A solution of 0.639 gr (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone while under constant agitation. A precipitate is formed which is then filtered and washed five times with 100 ml of acetone and lastly vacuum-dried for 24 hours at 30° C.

2.74 grs of the title compound are obtained. Quantitative determination of the ethoxy groups is carried out according to the method of R. H. Cundiff and P. C. Markunas (Anal. Chem. 33, 1028–1030 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 31

Preparation of the Partial Cortisone Ester (C21) of Cross-Linked Hyaluronic Acid (HY)
Product Description 20% of carboxy groups esterified with cortisone.

25% of carboxy groups used in internal esterification.

55% of carboxy groups salified with sodium.

6.21 gr of HY tetrabutylammonium salt with a molecular weight of 70,000 corresponding to 10 mEq of a monomeric unit are solubilized in 248 ml of DMSO at 25° C. 0.85 gr (2 mEq) 21-bromo-4-pregnene-17-$\alpha$-ol-3, 11, 20-trion and the resulting solution is kept for 24 hours at 30° C. 0.253 gr (2.5 mEq) of triethylamine are added and the resulting solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

4.5 grs of the title compound are obtained. Quantitative determination of cortisone, mild alkaline hydrolysis with a hydroalcoholic solution of $Na_2CO_3$ and extraction with chloroform, is carried out according to B.P.

Quantitative determination of the total ester groups is carried out according to the saponification method described on pp 169–172 of "Quantitative Organic Analysis Via Functional Groups" 4th Edition John Wiley and Sons Publication.

EXAMPLE 32

Preparation of the Mixed Ethanol and Cortisone Partial Ester (C21) of Cross-Linked Hyaluronic Acid (HY)
Product Description 20% of carboxy groups esterified with cortisone (C21).

25% of carboxy groups esterified with ethanol.

25% of carboxy groups used in internal esterification.

30% of carboxy groups salified with sodium.

6.21 gr of HY tetrabutylammonium salt with a molecular weight of 85.000 corresponding to 10 mEq of a monomeric unit are solubilized in 248 ml of DMSO at 25° C. 0.39 gr (2.5 mEq) of ethyl iodide are added and the resulting solution is kept at 30° C. for 12 hours. 0.85 gr (2 mEq) of 21-bromo-4-pregnene-17-$\alpha$-ol-3,11, 20-trion are added and the resulting solution is kept at 30° C. for 24 hours. 0.253 gr (2.5 mEq) of triethylamine are added and the resulting solution is agitated for 30 minutes.

A solution of 0.639 g (2.5 mEq) of 2-chloro-1-methyl pyridinium iodide in 60 ml of DMSO is slowly added drop by drop over a period of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

4.41 grs of the title compound are obtained. Quantitative determination of cortisone, mild alkaline hydrolysis with a hydroalcoholic solution of $Na_2CO_3$ and extraction with chloroform, is carried out according to B.P.

Quantitative determination of the ethoxy groups is carried out according to the method of R. H. Cundiff and P. C. Markunas (Anal. Chem. 33, 1028–1030 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 33

Preparation of the Mixed Ethanol and Cortisone Ester (C21) of Cross-Linked Hyaluronic Acid (HY)
Product Description
  20% of carboxy groups esterified with cortisone (C21).
  70% of carboxy groups esterified with ethanol.
  10% of carboxy groups used in internal esterification.

6.21 g of HY tetrabutylammonium salt with a molecular weight of 170,000 corresponding to 10 mEq of a monomeric unit are solubilized in 248 ml of DMSO at 25° C. 1.09 g (7 mEq) of ethyl iodide are added and the resulting solution is kept at 30° C. for 12 hours. 0.85 gr (2 mEq) of 21-bromo-4-pregnene-17-α-ol-3,11, 20-trion and the resulting solution is kept at 30° C. for 24 hours. 0.101 gr (1.0 mEq) of triethylamine are added and the resulting solution is agitated for 30 minutes.

A solution of 0.255 g (1.0 mEq) of 2-chloro-1-methyl pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml of acetone and lastly vacuum-dried for 24 hours at 30° C.

4.58 grs of the title compound are obtained. Quantitative determination of cortisone, mild alkaline hydrolysis with a hydroalcoholic solution of $Na_2CO_3$ and extraction with chloroform, is carried out according to B.P.

Quantitative determination of the ethoxy groups is carried out according to the method of R. H. Cundiff and P. C. Markunas (Anal. Chem. 33, 1028–1030 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 34

Preparation of the Partial Tetrabutylammonium Salt of Hyaluronic Acid (HY)
Product Description
  25% of carboxyls salified with tetrabutylammonium.
  75% of carboxyls in acid form.

4.0 gr of HY sodium salt with a molecular weight of 170,000, corresponding to 10 mEq of a monomeric unit, are solubilized in 400 ml of distilled $H_2O$, and then passed through a thermostatic column at 5° C., containing 15 ml of sulfonic resin (Dowex 50x8) in $H^+$ form. The sodium-free eluate, kept at a temperature of 5° C., is added to 25 ml of a solution of 0.1M of tetrabutylammonium hydroxide, while under constant agitation.

The resulting solution is frozen and freeze-dried.

EXAMPLE 35

Preparation of Cross-Linked Hyaluronic Acid Salt with Carteolol
Product Description
  25% of carboxy groups used in internal esterification.
  75% of carboxy groups with carteolol.

4.39 gr of partial tetrabutylammonium salt (25%) of hyaluronic acid corresponding to 10 mEq of a monomeric unit are solubilized in 248 ml of DMSO at 25° C., 0.253 gr (2.5 mEq) of triethylamine is added and the resulting solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml di acetone and lastly vacuum-dried for 24 hours at 30° C.

The precipitate is suspended in 400 ml of distilled water and cooled to 5° C.

2.19 gr (7.5 mEq) of basic carteolol are added and the whole is agitated for 30 minutes. The resulting mixture is freeze-dried.

5.8 grs of the title compound are obtained. Quantitative determination of the ester groups is carried out according to the saponification method described on pp 169–172 of "Quantitative Organic Analysis Via Functional Groups" 4th Edition John Wiley and Sons Publication.

Analytical determination of carteolol is carried out according to the method of S. Y. Chu [J. Pharmac. Sci. 67, 1623 (1978)].

EXAMPLE 36

Preparation with Kanamycin of the Salt of a Cross-Linked Hyaluronic Acid
Product Description
  25% of carboxy groups used in internal esterification.
  75% of carboxy groups with kanamycin.

4.39 gr of partial tetrabutylammonium salt (25%) of hyaluronic acid corresponding to 10 mEq of a monomeric unit are solubilized in 248 ml of DMSO at 25° C., 0.253 gr (2.5 mEq) of triethylamine are added and the resulting solution is agitated for 30 minutes.

A solution of 0.639 g (2.5 mEq) of 2-chloro-1-methyl-pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml di acetone and lastly vacuum-dried for 24 hours at 30° C.

The precipitate is suspended in 400 ml of distilled water and cooled to 5° C. after which a solution obtained by solubilizing 1.1 gr of Kanamycin sulfate (7.5 mEq) in 25 ml of distilled H₂O and eluting in a column containing 15 ml of quaternary ammonium resin (Dowex 1x8) OH— form is added, while agitation is maintained for 30 minutes. The resulting mixture is freeze-dried.

4.6 grs of the title compound are obtained. Quantitative determination of the ester groups is carried out according to the saponification method described on pp 169–172 of "Quantitative Organic Analysis Via Functional Groups" 4th Edition John Wiley and Sons Publication.

Microbiological quantitative determination of Kanamycin is carried out on *B. subtilis* 6633 in comparison to standard Kanamycin.

EXAMPLE 37

Preparation with Amikacin of a Cross-Linked Hyaluronic Acid Salt
Product Description
  25% of carboxy groups used in internal esterification.
  75% of carboxy groups with amikacin.

4.39 gr of partial tetrabutylammonium salt (25%) of hyaluronic acid corresponding to 10 mEq of a monomeric unit are solubilized in 248 ml of DMSO at 25° C., 0.253 gr (2.5 mEq) of triethylamine are added and the resulting solution is agitated for 30 minutes.

A solution of 0.639 gr (2.5 mEq) of 2-chloro-1-methyl-piridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml of acetone and lastly vacuum-dried for 24 hours at 30° C.

The precipitate is suspended in 400 ml of distilled water and cooled to 5° C.

1.1 gr (7.5 mEq) of basic amikacin are added while under constant agitation for 30 minutes. The resulting mixture is freeze-dried.

4.8 grs of the title compound are obtained. Quantitative determination of the ester groups is carried out according to the saponification method described on pp 169–172 of "Quantitative Organic Analysis Via Functional Groups" 4th Edition John Wiley and Sons Publication.

Quantitative determination of amikacin is carried out microbiologically on *S. aureus* 29737, compared to standard Amikacin.

EXAMPLE 38

Preparation of the Partial Ethyl Ester of Cross-Linked Hyaluronic Acid (HY)
Product Description
  50% of carboxy groups esterified with ethanol.
  10% of carboxy groups used in internal esterification.
  40% of carboxy groups salified with sodium.

6.21 gr of HY tetrabutylammonium salt with a molecular weight of 85.000 corresponding to 10 mEq of a monomeric unit are solubilized in 248 ml of DMSO at 25° C., 0.780 gr (5.0 mEq) of ethyl iodide are added and the solution is kept for 12 hours at 30° C. 0.118 gr (1 mEq) of pyridine chloride are added and the resulting solution is agitated for 30 minutes.

A solution of 0.16 g (1 mEq) of N-benzyl-N'-ethyl carbodiimmide in 20 ml of DMSO is slowly added drop by drop over a time interval of 1 hour and the mixture is kept for 45 hours at 30° C.

A solution is then added which is formed of 100 ml of water and 2.5 of sodium chloride and the resulting mixture is then poured slowly into 750 ml of acetone, maintaining continual agitation. A precipitate is formed which is then filtered and washed three times with 100 ml of acetone/H₂O 5:1 and three times with 100 ml of acetone and lastly vacuum-dried for 24 hours at 30° C.

3.85 grs of the title compound are obtained. Quantitative determination of the ethoxy groups is carried out according to the method of R. H. Cundiff and P. C. Markunas (Anal. Chem. 33, 1028–1930 (1961). Quantitative determination of the total ester groups is carried out according to the saponification method described on pp 169–172 of "Quantitative Organic Analysis Via Functional Groups" 4th Edition John Wiley and Sons Publication.

EXAMPLE 39

Preparation of Cross-Linked Hyaluronic Acid (HY)
Product Description
  10% of carboxy groups used in internal esterification.
  90% of carboxy groups salified with sodium.

6.21 gr of HY tetrabutylammonium salt with a molecular weight of 170,000 corresponding to 10 mEq of a monomeric unit are solubilized in 248 ml of DMSO at 25° C., 0.118 gr (1 mEq) of pyridine chloride are added and the resulting solution is agitated for 30 minutes.

A solution of 0.16 g (1 mEq) of N-benzyl-N'-ethyl carbodiimmide in 20 ml of DMSO is slowly added drop by drop over a time interval of 1 hour and the mixture is kept at a temperature of 30° C. for 45 hours.

A solution made up of 100 ml of water and 2.5 of sodium chloride is added and the resulting mixture is slowly poured into 750 ml of acetone, maintaining continual agitation. A precipitate is formed which is then filtered and washed three times with 100 ml of acetone/H₂O 5:1 and three times with 100 ml of acetone finally vacuum-dried for 24 hours at a temperature of 30° C.

3.9 grs of the title compound are obtained. Quantitative determination of the total ester groups is carried out according to the saponification method described on pp 169–172 of "Quantitative Organic Analysis Via Functional Groups" 4th Edition John Wiley and Sons Publication.

The above preparation examples are only exemplary of the various cross-linked polysaccharides according to the invention. Other specifically desired products can be prepared by following the above described procedures, but substituting as appropriate other starting materials and/or reactants to result in the desired cross-linked product. Thus, for instance, cross-linked derivatives based on carboxymethylcellulose or carboxymethyl starch can be prepared by following the steps set forth in above Examples 21–30, but substituting for carboxymethylchitin in those examples alternative starting materials based on carboxymethylcellulose or carboxymethyl starch.

As discussed above, the new polysaccharide esters of the invention are useful for the preparation of pharmaceutical formulations and new medical articles. The following are particular exemplary pharmaceutical preparations according to the invention.

Formulation 1

Collirium containing cortisone of which 100 ml contain:

| | |
|---|---|
| partial and mixed ester of hyaluronic acid with cortisone and ethanol (Ex. 32) | gr. 0.300 |
| ethyl p. hydroxybenzoate | gr. 0.010 |
| methyl p. hydroxybenzoate | gr. 0.050 |

-continued

| | |
|---|---|
| sodium chloride | gr. 0.900 |
| water for injectable preparation/q.b.a. | ml. 100 |

Formulation 2

Cream containing a partial ester of hyaluronic acid with ethanol of which 100 gr. contain:

| | |
|---|---|
| partial ester of hyaluronic acid with ethanol (Ex. 9) | gr. 0.2 |
| polyethyleneglycol monostearate 400 | gr. 10.000 |
| Cetiol V | gr. 5.000 |
| Lanette SX | gr. 2.000 |
| Paraoxybenzoate of methyl | gr. 0.075 |
| Paraoxybenzoate of propyl | gr. 0.050 |
| Sodium dihydroacetate | gr. 0.100 |
| Glycerine F.U. | gr. 1.500 |
| Sorbitol 70 | gr. 1.500 |
| Test cream | gr. 0.050 |
| Water for injectable preparation/q.b.a. | gr. 100.00 |

Formulation 3

Cream containing a partial ester of carboxymethylchitin with ethyl alcohol, of which 100 gr. contain:

| | |
|---|---|
| partial ester of carboxymethylchitin (Ex. 29) with ethyl alcohol | gr. 0.2 |
| Polyethyleneglycol monostearate 400 | gr. 10.000 |
| Cetiol V | gr. 5.000 |
| Lanette SX | gr. 2.000 |
| Paraoxybenzoate of methyl | gr. 0.075 |
| Paraoxybenzoate of propyl | gr. 0.050 |
| Sodium dihydroacetate | gr. 0.100 |
| Glycerine F.U. | gr. 1.500 |
| Sorbitol 70 | gr. 1.500 |
| Test cream | gr. 0.050 |
| Water for injectable preparations/q.b.a. | gr. 100.00 |

The following preparations exemplify the medical articles according to the invention containing the alginic esters.

EXAMPLE 40

Preparation of Films Using Cross-Linked Esters of Carboxymethylcellulose

A solution is prepared in dimethylsulfoxide of the cross-linked n-propyl ester of carboxymethylcellulose.

By means of a stratifier, a thin layer of solution is spread on a glass sheet; the thickness must be 10 times greater than the final thickness of the film. The glass sheet is immersed in ethanol which absorbs the dimethylsulfoxide but does not solubilize the carboxymethylcellulose ester which becomes solid. The film is detached from the glass sheet, is repeatedly washed with ethanol, then with water and then again with ethanol.

The resulting sheet is dried in a press for 48 hours at 30° C.

EXAMPLE 41

Preparation of Threads Using Cross-Linked Esters of Carboxymethylcellulose

A solution is prepared in dimethylsulfoxide of the cross-linked benzyl ester of carboxymethylcellulose. The solution thus obtained is pressed by means of a pump through a threader with 0.5 mm holes.

The threader is immersed in ethanol/dimethylsulfoxide 80:20 (this concentration is kept constant by continuous addition of ethanol); when the solution in dimethylsulfoxide is soaked in this way it tends to lose most of the dimethylsulfoxide and the thread solidifies.

The thread is stretched while it still has a content of dimethylsulfoxide, is then repeatedly stretched and washed with ethanol. The thread is dried in nitrogen current.

EXAMPLE 42

Preparation of a Spongy Material Made with Cross-Linked Esters of Carboxymethylchitin The cross-linked benzyl ester of carboxymethylchitin in which all the carboxylic groups are esterified are dissolved in dimethylsulfoxide. To each 10 ml of solution prepared, a mixture of 31.5 g of sodium chloride with a degree of granularity corresponding to 300µ, 1.28 g of sodium bicarbonate and 1 g of citric acid is added and the whole is homogenized in a mixer.

The pasty mixture is stratified in various ways, for instance by means of a mange consisting of two rollers which turn opposite each other at an adjustable distance between the two. Regulating this distance the paste is passed between the rollers together with a strip of silicone paper which acts as a support to the layer of paste thus formed. The layer is cut to the desired dimensions of length and breadth, removed from the silicone, wrapped in filter paper and emerged in a suitable solvent, such as water. The sponges thus obtained are washed with a suitable solvent such as water and possibly sterilized with gamma rays.

EXAMPLE 43

Preparation of a Spongy Material Made With Cross-Linked Esters of Carboxymethylchitin In the manner described in Example 42, it is possible to prepare spongy materials with other carboxymethylchitin esters. In the place of dimethylsulfoxide it is possible to use, if desired, any other solvent capable of dissolving the chosen ester. In the place of sodium chloride it is possible to use any other solid compound which is insoluble in the solvent used to dissolve the carboxymethylchitin ester, but which is however soluble in the solvent used to dissolve the carboxymethylchitin ester after the above mentioned mechanical treatment, and finally which has the correct degree of granularity to obtain the type of pores desired in the sponge material.

In the place of sodium bicarbonate and citric acid it is possible to use other couples of similar compounds, that is, compounds which react to each other in suspension or solution of the solvent used to dissolve carboxymethylchitin in such a way as to form a gas, such as carbon dioxide, which has the effect of producing a less compact spongy material. In this way it is possible to use, in the place of sodium bicarbonate, other bicarbonates or alkaline or alkaline earth carbonates and in the place of citric acid other acids in solid form, such as tartaric acid.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. Cross-linked carboxy acidic polysaccharides or a salt thereof having auto-crosslinking bonds consisting of direct ester and lactonic bonds formed between carboxyl groups of one acidic polysaccharide and hydroxyl groups of the same polysaccharide molecule and/or to hydroxyl groups of different polysaccharide molecules.

2. Cross-linked acidic polysaccharides according to claim 1, wherein said polysaccharides are selected from the group consisting of hyaluronic acid, alginic acid, carboxymethylcellulose, and carboxymethylchitin.

3. Cross-linked acidic polysaccharides according to one of claims 1 and 2, wherein all of the carboxyl functions of said polysaccharides are ester bonded to a hydroxyl group.

4. Cross-linked acidic polysaccharides according to claim 1, wherein the percentage of said first portion of carboxyl groups involved in cross-linking to the total number of carboxyl groups in said polysaccharide ranges between 1% and 60%.

5. Cross-linked acidic polysaccharides according to claim 4, wherein the percentage of cross-linking ranges between 15% and 30%.

6. Cross-linked acidic polysaccharides according to claim 1, wherein a first portion of the carboxyl groups of said polysaccharides are cross-linked to hydroxyl groups of the same or different polysaccharide molecule and a second portion of carboxyl groups of said polysaccharide are esterified with a mono- or polyvalent alcohol.

7. Cross-linked acidic polysaccharides according to claim 6, wherein said alcohol is a member selected from the group consisting of aliphatic, araliphatic, cycloaliphatic and heterocyclic alcohols.

8. Cross-linked acidic polysaccharides according to claim 7, wherein said alcohols of the aliphatic series have a maximum of 34 carbon atoms and may be substituted by one or two functional groups selected from the group consisting of amino, hydroxy, mercapto, aldehydo, ketal, carboxy, hydrocarbyl, and dihydrocarbylamino, ether, ester, thioester, acetel, ketal, carbamidic groups and carbamidic groups substituted by one or more alkyl groups, wherein the hycrocarbyl radicals in these groups have a maximum of 6 functionally modified carbon atoms, and alcohols of the aliphatic series may be interrupted in the carbon atom chain by heteroatoms selected from the group consisting of oxygen, sulfur and nitrogen.

9. Cross-linked acidic polysaccharides according to claim 8, wherein said alcohol is an alcohol with a maximum of 32 carbon atoms and, wherein the hydrocarbyl radicals of the amine, ether, ester, thioether, thioester, acetel, and ketal groups are alkyl groups with a maximum of 4 carbon atoms; the hydrocarbyl groups of the esterified carboxy groups and substituted carbamidic groups are alkyl groups with the same number of carbon atoms; and the substituted amino or carbamidic groups are alkyleneamino or alkylenecarbamidic groups with a maximum of 8 carbon atoms.

10. Cross-linked acidic polysaccharides according to claim 9, wherein said alcohol is ethyl, propyl, isopropyl, N-butyl, isobutyl, tert-butyl alcohols, an amyl, pentyl, hexyl or octyl alcohol.

11. Cross-linked acidic polysaccharides according to claim 9, wherein said alcohol component is ethyleneglycol, propyleneglycol, butyleneglycol or glycerin.

12. Cross-linked acidic polysaccharides according to claim 9, wherein said alcohol is tartronic alcohol, lactic acids, glycolic acid, malic acid, a tartaric acid or citric acid.

13. Cross-linked acidic polysaccharides according to claim 7, wherein said alcohols of the araliphatic series have only one benzene residue and have an aliphatic chain with a maximum of 4 carbon atoms and wherein the benzene residue may be substituted by between 1 and 3 methyl or hydroxy groups, or by halogen atoms, and wherein the aliphatic chain may be substituted by one or two functions selected from the group consisting of free amino groups, mono- or diethyl groups pyrrolidine and piperidine groups.

14. Cross-linked acidic polysaccharides according to claim 7, wherein said alcohols of the cycloaliphatic or aliphatic-cycloaliphatic series are mono- or polycyclic hydrocarbons with a maximum of 34 carbon atoms.

15. Cross-linked acidic polysaccharides according to claim 7, wherein said heterocyclic alcohols are mono- or polycyclic cycloaliphatic or aliphatic cycloaliphatic alcohols interrupted in their carbon atom chain or ring by one or more heteroatoms selected from the group consisting of nitrogen, oxygen and sulfur.

16. Cross-linked acidic polysaccharides according to claim 7, wherein said heterocyclic alcohols are selected from the group consisting of alkaloids, phenylethylamines, phenothiazine drugs, thioxanthene drugs, anticonvulsivants, antipsychotics, antiemetics, analgesics, hypnotics, anorexics, tranquillizers, muscle relaxants, coronary vasodilators, adrenergic blockers, narcotic blockers, antineoplastics, antibiotics, antivirals, peripheral vasodilators, carbonic anhydrase inhibitors, antiasthmatics, antiinflammatories and sulfamidics.

17. A salt of a cross-linked polysaccharide according to claim 1 with an alkaline or alkaline earth metal, magnesium, aluminum or an amine.

18. A salt according to claim 17, with sodium or ammonium.

19. A salt according to claim 17, wherein said amine is an aliphatic, araliphatic, cycloaliphatic or heterocyclic amine.

20. A salt according to claim 19, wherein said amine is a therapeutically acceptable base.

21. A salt according to claim 19, wherein said amine is a therapeutically active base.

22. A salt according to claim 21, wherein said amine is selected from the group consisting of: alkaloids, peptides, phenothiazine, benzodiazepine, thioxanthene, hormones, vitamins, anticonvulsivants, antipsychotics, antiemetics, anesthetics, hypnotics, anorexics, tranquilizers, muscle relaxants, coronary vasodilators, antineoplastics, antibiotics, antibacterials, antivirals, antimalarials, carbonic anhydrase inhibitors, nonsteroid antiinflammatories, vasoconstrictors, cholinergic agonists, cholinergic blockers, adrenergic agonists, adrenergic blockers, and narcotic blockers.

23. A salt according to claim 17, wherein said amine is pharmacologically inactive and is selected from the group consisting of mono-, di-and tri-alkylamines with a maximum of 18 carbon atoms, arylalkylamines with a maximum of 18 carbon atoms in the aliphatic part and a benzene group as an aromatic part, optionally substituted by between 1 and 3 methyl groups or halogen atoms or hydroxyl groups, alkyleneamines with cycles of between 4 and 6 carbon atoms optionally interrupted in the cycle by heteroatoms chosen from the group consisting of O and S, and amines of all these types substituted by amino or hydroxy functions.

24. Cross-linked acidic polysaccharides or a salt thereof according to claim 2, wherein said polysaccharide is hyaluronic acid.

25. Cross-linked acidic polysaccharides or a salt thereof according to claim 2, wherein said polysaccharide is alginic acid.

26. Cross-linked acidic polysaccharides or a salt thereof according to claim 2, wherein said polysaccharide is carboxymethylchitin.

27. A cross-linked polysaccharide according to claim 24 which is a totally or partially cross-linked hyaluronic acid, wherein said partially cross-linked hyaluronic acid includes a portion of carboxyl groups esterified with a lower aliphatic alcohol, and optionally includes a portion of carboxyl groups salified with an alkaline metal.

28. A compound according to claim 27, selected from the group consisting of:
- hyaluronic acid cross-linked to an extent of 1% of the carboxy groups and salified with sodium to an extent of 99%;
- hyaluronic acid cross-linked to an extent of 5% of the carboxy groups and salified with sodium to an extent of 95%;
- hyaluronic acid cross-linked to an extent of 10% of the carboxy groups and salified with sodium to an extent of 90%;
- hyaluronic acid cross-linked to an extent of 25% of the carboxy groups and salified with sodium to an extent of 75%;
- hyaluronic acid cross-linked to an extent of 50% of the carboxy groups and salified with sodium to an extent of 50%;
- hyaluronic acid cross-linked to an extent of 75% of the carboxy groups and salified with sodium to an extent of 25%;
- hyaluronic acid cross-linked to an extent of 100% of the carboxy groups;
- hyaluronic acid cross-linked to an extent of 25% of the carboxy groups, esterified to an extent of 25% with ethanol and salified with sodium to an extent of 50%;
- hyaluronic acid cross-linked to an extent of 25% of the carboxy groups, esterified to an extent of 50% with ethanol and salified with sodium to an extent of 25%; and
- hyaluronic acid cross-linked to an extent of 25% of the carboxy groups and esterified with ethanol to an extent of 75%.

29. A cross-linked polysaccharide according to claim 25, which is a totally or partially cross-linked alginic acid, wherein said partially cross-linked alginic acid includes a portion of carboxy groups esterified with a lower aliphatic alcohol, and optionally includes a portion of carboxy groups salified with an alkaline metal.

30. A compound according to claim 29, selected from the group consisting of:
- alginic acid cross-linked to an extent of 1% of the carboxy groups and salified with sodium to an extent of 99%;
- alginic acid cross-linked to an extent of 5% of the carboxy groups and salified with sodium to an extent of 95%;
- alginic acid cross-linked to an extent of 10% of the carboxy groups and salified with sodium to an extent of 90%;
- alginic acid cross-linked to an extent of 25% of the carboxy groups and salified with sodium to an extent of 75%;
- alginic acid cross-linked to an extent of 50% of the carboxy groups and salified with sodium to an extent of 50%;
- alginic acid cross-linked to an extent of 75% of the carboxy groups and salified with sodium to an extent of 25%;
- alginic acid cross-linked to an extent of 100% of the carboxy groups;
- alginic acid cross-linked to an extent of 25% of the carboxy groups, esterified with ethanol to an extent of 25% and salified with sodium to an extent of 50%;
- alginic acid cross-linked to an extent of 25% of the carboxy groups, esterified with ethanol to an extent of 50% and salified with sodium to an extent of 25%; and
- alginic acid cross-linked to an extent of 25% of the carboxy groups ed esterified to an extent of 75% with ethanol.

31. A compound according to claim 26 which is a totally or partially cross-linked carboxymethylchitin, wherein said partially cross-linked carboxymethylchitin includes a portion of carboxy groups esterified with a lower aliphatic alcohol, and optionally includes a portion of carboxy groups salified with an alkaline metal.

32. A compound according to claim 31 selected from the group consisting of:
- carboxymethylchitin cross-linked to an extent of 1% of the carboxy groups and salified with sodium to an extent of 99%;
- carboxymethylchitin cross-linked to an extent of 5% of the carboxy groups salified with sodium to an extent of 95%;
- carboxymethylchitin cross-linked to an extent of 10% of the carboxy groups and salified with sodium to an extent of 90%;
- carboxymethylchitin cross-linked to an extent of 10% of the carboxy groups and salified with sodium to an extent of 90%;
- carboxymethylchitin cross-linked to an extent of 25% of the carboxy groups and salified with sodium to an extent of 75%;
- carboxymethylchitin cross-linked to an extent of 50% of the carboxy groups and salified with sodium to an extent of 50%;
- carboxymethylchitin cross-linked to an extent of 75% of the carboxy groups and salified to an extent of 25%; and
- carboxymethylchitin cross-linked to an extent of 100% of the carboxy groups.

33. A compound according to claim 31 selected from the group consisting of:
- carboxymethylchitin cross-linked to an extent of 25% of the carboxy groups, esterified to an extent of 25% with ethanol and salified to an extent of 50%;
- carboxymethylchitin cross-linked to an extent of 25% of the carboxy groups, esterified with ethanol to an extent of 50% and salified with sodium to an extent of 25%; and
- carboxymethylchitin cross-linked to an extent of 25% of the carboxy groups and esterified with ethanol to an extent of 75%.

34. A compound according to claim 24 selected from the group consisting of:
- hyaluronic acid cross-linked to an extent of 25% of the carboxy groups, esterified to an extent of 20% with cortisone and salified with sodium to an extent of 55%;
- hyaluronic acid cross-linked to an extent of 25% of the carboxy groups, esterified with cortisone to an extent of 20% and with ethanol to an extent of 25% and salified with sodium to an extent of 30%;
- hyaluronic acid cross-linked to an extent of 10% of the carboxy groups, esterified with cortisone to an extent of 20% and with ethanol to an extent of 70%;
- hyaluronic acid cross-linked to an extent of 25% of the carboxy groups and salified with carteololo to an extent of 75%;

hyaluronic acid cross-linked to an extent of 25% of the carboxy groups and salified to an extent of 75% with kanamycin; and hyaluronic acid cross-linked to an extent of 25% of the carboxy groups and salified with amikacin to an extent of 75%.

35. A pharmaceutical composition comprising as an active ingredient a compound according to claim 21 together with an excipient.

36. A medicament comprising:
   (1) a pharmacologically active substance or a mixture of pharmacologically active substances; and
   (2) a vehicle comprised of a cross-linked polysaccharide according to claim 1.

37. A medicament according to claim 36, in which component (1) is a substance for oral, parenteral or topical use.

38. A medicament according to claim 37, in which the polysaccharide of component (2) is hyaluronic acid.

39. A medicament according to claim 37, wherein the component (1) is an anesthetic, analgesic, antiinflammatory, vasocontrictory antibiotic/antibacterial or antiviral agent.

40. A cosmetic article containing a cross-linked acidic polysaccharide according to claim 1.

41. A sanitary or surgical article containing a cross-linked acidic polysaccharide according to claim 1.

42. A sanitary or surgical article according to claim 41, comprised of threads or films of a cross-linked product of an acidic polysaccharide.

43. A sanitary or surgical article according to claim 41, comprised of capsules for the subcutaneous implantation of medicaments.

44. A sanitary or surgical article according to claim 41, comprised of microcapsules for subcutaneous, intramuscular or intravenous injection.

45. A sanitary or surgical article according to claim 41, comprised of solid inserts adapted to be removed after a certain length of time.

46. A sanitary or surgical article according to claim 41, comprised of sponges for the medication of wounds and lesions.

47. A sanitary or surgical article according to claim 41, wherein the polysaccharide is hyaluronic acid.

48. A sanitary or surgical article according to claim 41, wherein the polysaccharide is alginic acid.

49. A process for the preparation of threads or films of auto-cross-linked acidic polysaccharide of claim 1 which comprises:
   (a) dissolving an auto-cross-linked acidic polysaccharide in a first organic solvent;
   (b) forming said solution of auto-cross-linked acidic polysaccharide into a sheet or thread form;
   (c) eliminating said solvent by treatment with a second organic or aqueous solvent which is soluble in said first organic solvent.

50. A process according to claim 49, wherein dimethylsulfoxide is used as said first organic solvent.

51. A process according to claim 49, wherein hexafluoroisopropanol is used as said first organic solvent and is eliminated by treatment with a flow of heated inert gas.

52. A process for the preparation of auto-cross-linked carboxy acidic polysaccharides of claim 1 which comprises:
   (a) treating an acidic polysaccharide with an activating agent to activate carboxy groups in said polysaccharide to form intermediate activated polysaccharide derivatives; and
   (b) subjecting said intermediate activated polysaccharide derivatives to heat or irradiation to produce auto-cross-linked carboxy acidic polysaccharides.

53. A process according to claim 52, wherein at least a portion of the carboxy groups in said acidic polysaccharides are salified.

54. A process according to claim 53, wherein said at least a portion of carboxy groups are salified with an alkaline or alkaline earth metal, or with a quaternary ammonium.

55. A process according to claim 52, wherein said treatment with an activating agent is performed in the presence of a catalyst.

56. A process according to claim 52, wherein a portion of the carboxy groups in said acidic polysaccharide are esterified with a mono- or polyvalent alcohol.

57. A process according to claim 52, wherein said activating agent is a carbodiimide, ethoxyacetylene, Woodward's reagent, or chloroacetonitryl.

58. A process according to claim 52, wherein said activating agent is a 2-halogen-N-alkyl-pyridinium salt, in which the halogen is selected from the group consisting of chlorine and bromine and the alkyl has a maximum of 6 carbon atoms.

59. A process according to claim 58, wherein said activating agent is a chloride of 2-chloro-N-methyl-pyridine and reacts with a tetrabutylammonium salt of the polysaccharide in the presence of a tertiary amine base.

60. A process according to claim 52, wherein the reaction is carried out in an organic aprotic solvent.

61. A process according to claim 60, wherein said organic aprotic solvent is a dialkylsulfoxide or a dialkylamide of a lower aliphatic alcohol with an alkyl having a maximum of 6 carbon atoms.

62. A process according to claim 61, wherein dimethylsulfoxide is used as said solvent.

63. A process according to claim 52, wherein the reaction is carried out within a temperature range of between 0° C. and 150° C.

64. A process according to claim 63 in which the reaction is carried out at room temperature.

65. A process according to claim 52, wherein subsequent to said cross-linking reaction, at least a portion of any remaining free carboxyl groups in said cross-linked acidic polysaccharide are salified or esterified with a mono- or polyvalent alcohol.

* * * * *